United States Patent
Farquhar et al.

(10) Patent No.: US 10,993,650 B2
(45) Date of Patent: *May 4, 2021

(54) SYSTEM FOR DETERMINING NERVE DIRECTION TO A SURGICAL INSTRUMENT

(71) Applicant: NuVasive, Inc., San Diego, CA (US)

(72) Inventors: Allen Farquhar, Portland, OR (US); James E. Gharib, San Diego, CA (US); Norbert Kaula, Arvada, CO (US); Jeffrey J. Blewett, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 745 days.

This patent is subject to a terminal disclaimer.

(21) Appl. No.: 14/865,683

(22) Filed: Sep. 25, 2015

(65) Prior Publication Data

US 2016/0143556 A1    May 26, 2016

Related U.S. Application Data

(63) Continuation of application No. 13/427,760, filed on Mar. 22, 2012, now abandoned, which is a continuation of application No. 11/182,545, filed on Jul. 15, 2005, now Pat. No. 8,147,421, which is a continuation of application No. PCT/US03/02056, filed on Jan. 15, 2003.

(51) Int. Cl.
*A61B 5/389* (2021.01)
*A61B 5/05* (2021.01)
*A61B 5/00* (2006.01)
*A61B 5/296* (2021.01)
*A61B 90/00* (2016.01)

(52) U.S. Cl.
CPC .............. *A61B 5/389* (2021.01); *A61B 5/05* (2013.01); *A61B 5/296* (2021.01); *A61B 5/4893* (2013.01); *A61B 90/04* (2016.02)

(58) Field of Classification Search
None
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |

(Continued)

FOREIGN PATENT DOCUMENTS

| | | |
|---|---|---|
| DE | 299 08 259 | 7/1999 |
| EP | 0 759 307 | 2/1997 |

(Continued)

OTHER PUBLICATIONS

"Brackmann II EMG System", Medical Electronics, (1999), 4 pages.

(Continued)

*Primary Examiner* — Matthew Kremer

(57) ABSTRACT

A system performs surgical procedures and assessments. The system includes the use of neurophysiology-based monitoring to determine nerve proximity and nerve direction to surgical instruments employed in accessing a surgical target site.

30 Claims, 25 Drawing Sheets

(56) References Cited

U.S. PATENT DOCUMENTS

| | | |
|---|---|---|
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,611,597 A | 9/1986 | Kraus |
| 4,616,660 A | 10/1986 | Johns |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,811,742 A * | 3/1989 | Hassel ............ A61B 5/0488 128/905 |
| 4,892,105 A | 1/1990 | Prass |
| 4,913,134 A | 4/1990 | Luque |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,125,406 A | 6/1992 | Goldstone et al. |
| 5,127,403 A | 7/1992 | Brownlee |
| 5,161,533 A | 11/1992 | Prass et al. |
| 5,196,015 A | 3/1993 | Neubardt |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A * | 2/1994 | Raymond ............ A61B 5/05 600/554 |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,474,057 A | 12/1995 | Makower |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,509,893 A | 4/1996 | Pracas |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,248 A | 10/1996 | Matthews |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,601,608 A | 2/1997 | Mouchawar |
| 5,623,925 A * | 4/1997 | Swenson ............ A61B 5/0205 600/301 |
| 5,630,813 A | 5/1997 | Kieturakis |
| 5,667,508 A | 9/1997 | Errico et al. |
| 5,671,752 A | 9/1997 | Sinderby et al. |
| 5,681,265 A | 10/1997 | Maeda et al. |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron |
| 5,797,854 A | 8/1998 | Hedgecock |
| 5,806,522 A | 9/1998 | Katims |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,935,131 A | 8/1999 | Bonutti |
| 5,938,688 A | 8/1999 | Schiff |
| 5,947,964 A | 9/1999 | Eggers et al. |
| 5,976,094 A | 11/1999 | Gozani et al. |
| 6,004,262 A | 12/1999 | Putz et al. |
| 6,011,985 A | 1/2000 | Athan et al. |
| 6,024,696 A | 2/2000 | Hoftman et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Tumer et al. |
| 6,138,681 A | 10/2000 | Chen et al. |
| 6,139,493 A | 10/2000 | Koros et al. |
| 6,139,545 A | 10/2000 | Utley |
| 6,146,335 A | 11/2000 | Gozani |
| 6,161,047 A | 12/2000 | King et al. |
| 6,181,961 B1 | 1/2001 | Prass |
| 6,188,929 B1 * | 2/2001 | Giordano ............ A61N 1/08 607/59 |
| 6,196,969 B1 | 3/2001 | Bester et al. |
| 6,206,826 B1 | 3/2001 | Mathews et al. |
| 6,224,549 B1 | 5/2001 | Drongelen |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,292,701 B1 * | 9/2001 | Prass ............ A61N 1/0551 607/116 |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,393,325 B1 | 5/2002 | Mann et al. |
| 6,425,859 B1 | 7/2002 | Foley et al. |
| 6,425,901 B1 | 7/2002 | Zhu et al. |

(56) References Cited

U.S. PATENT DOCUMENTS

| | | |
|---|---|---|
| 6,450,952 B1 | 9/2002 | Rioux et al. |
| 6,451,015 B1 | 9/2002 | Rittman, III et al. |
| 6,466,817 B1 | 10/2002 | Kaula et al. |
| 6,500,128 B2 | 12/2002 | Marino |
| 6,507,755 B1 | 1/2003 | Marino et al. |
| 6,535,759 B1 | 3/2003 | Epstein et al. |
| 6,564,078 B1 | 5/2003 | Marino et al. |
| 6,579,244 B2 | 6/2003 | Goodwin |
| 6,582,441 B1 | 6/2003 | He et al. |
| 6,585,638 B1 | 7/2003 | Yamamoto |
| 6,618,626 B2 | 9/2003 | West, Jr. et al. |
| 6,620,157 B1 | 9/2003 | Dabney et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,902,569 B2 | 6/2005 | Parmer et al. |
| 6,926,728 B2 | 8/2005 | Zucherman et al. |
| 6,929,606 B2 | 8/2005 | Ritland |
| 6,945,933 B2 | 9/2005 | Branch et al. |
| 6,951,538 B2 | 10/2005 | Ritland |
| 7,047,082 B1 | 5/2006 | Schrom |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,207,949 B2 | 4/2007 | Miles et al. |
| 7,258,688 B1 | 8/2007 | Shah et al. |
| 7,294,127 B2 | 11/2007 | Leung et al. |
| 7,310,546 B2 | 12/2007 | Prass |
| 7,473,222 B2 | 1/2009 | Dewey et al. |
| 7,481,766 B2 | 1/2009 | Lee et al. |
| 7,522,953 B2 | 4/2009 | Kaula et al. |
| 7,582,058 B1 | 9/2009 | Miles et al. |
| 7,643,884 B2 | 1/2010 | Pond et al. |
| 7,657,308 B2 | 2/2010 | Miles et al. |
| 7,664,544 B2 | 2/2010 | Miles et al. |
| 7,691,057 B2 | 4/2010 | Miles et al. |
| 7,819,801 B2 | 10/2010 | Miles et al. |
| 8,050,769 B2 | 11/2011 | Gharib et al. |
| 8,137,284 B2 | 3/2012 | Miles et al. |
| 8,147,421 B2 * | 4/2012 | Farquhar ............ A61B 5/0488 600/546 |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0072686 A1 | 6/2002 | Hoey et al. |
| 2002/0116036 A1* | 8/2002 | Daignault, Jr. .......... A61N 1/08 607/59 |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0078618 A1 | 4/2003 | Fey et al. |
| 2003/0105503 A1 | 6/2003 | Marino |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1 | 4/2005 | Lee et al. |
| 2005/0080418 A1 | 4/2005 | Simonson et al. |
| 2005/0119660 A1 | 6/2005 | Burlion |
| 2005/0149035 A1 | 7/2005 | Pimenta et al. |
| 2005/0182454 A1 | 8/2005 | Gharib et al. |
| 2005/0256582 A1 | 11/2005 | Ferree |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0015612 A1 | 1/2008 | Urmey |
| 2008/0039914 A1 | 2/2008 | Cory et al. |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2009/0192403 A1 | 7/2009 | Gharib et al. |
| 2009/0204016 A1 | 8/2009 | Gharib et al. |
| 2009/0204176 A1 | 8/2009 | Miles et al. |
| 2009/0209879 A1 | 8/2009 | Kaula et al. |

FOREIGN PATENT DOCUMENTS

| | | |
|---|---|---|
| EP | 0 972 538 | 1/2000 |
| FR | 2 795 624 | 1/2001 |
| FR | 2 796 846 | 2/2001 |
| JP | 2001-299718 | 10/2001 |
| WO | WO 00/38574 | 7/2000 |
| WO | WO 00/66217 | 11/2000 |
| WO | WO 00/67645 | 11/2000 |
| WO | WO 01/03604 | 1/2001 |
| WO | WO 01/37728 | 5/2001 |
| WO | WO 03/005887 | 1/2003 |
| WO | WO 03/026482 | 4/2003 |
| WO | WO 03/037170 | 5/2003 |
| WO | WO 2004/012809 | 2/2004 |
| WO | WO 2005/013805 | 2/2005 |
| WO | WO 2006/084193 | 8/2006 |

OTHER PUBLICATIONS

"Electromyography System", International Search Report, International Application No. PCT/US00/32329, (dated Apr. 27, 2001), 9 pages.

"Multi-Channel Stimulation Threshold Detection Algorithm for Use in Neurophysiology Monitoring," International Search Report from International Application No. PCT/US06/37013, dated Mar. 19, 2007, 10 pages.

"Nerve Proximity and Status Detection System and Method," International Search Report from International Application No. PCT/US01/18606, dated Oct. 18, 2001, 6 pages.

"Neurovision SE Nerve Locator/Monitor", RLN Systems, Inc. Operators Manual, (1999), 22 pages.

"New data analyzer combines the functions of six instruments in one unit," News Release, Nov. 11, 1987, 3 pages.

"NIM-Response, so advanced . . . yet so simple," XoMed, Inc., 1999, 12 pages.

"NuVasive's spine surgery system cleared in the US," Pharm & Medical Industry Week, Dec. 10, 2001, 1 page.

"Relative Nerve Movement and Status Detection System and Method," International Search Report from International Application No. PCT/US01/18579, dated Jan. 15, 2002, 6 pages.

"Risk Capital Funds," Innovation, Mar. 6, 1990, 172: 3 pages.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Neurophysiologic Assessments During Spine Surgery," International Search Report from International Application No. PCT/US06/03966, dated Oct. 23, 2006, 5 pages.

"Systems and Methods for Performing Percutaneous Pedicle Integrity Assessments," International Search Report from International Application No. PCT/US02/35047, dated Aug. 11, 2003, 5 pages.

(56) References Cited

OTHER PUBLICATIONS

"Systems and Methods for Performing Surgery Procedures and Assessments," International Search Report from International Application No. PCT/US02/30617, dated Jun. 5, 2003, 4 pages.

"The Brackmann II EMG Monitoring System", Medical Electronics Co. Operator's Manual Version 1.1, (1995), 50 pages.

"The Nicolet Viking IV", Nicolet Biomedical Products, (1999), 6 pages.

Anderson, D. G., et al., "Pedicle screws with high electrical resistance: a potential source of error with stimulus-evoked EMG", Spine. 27(14), Department of Orthopaedic of Virginia, (Jul. 15, 2002), 1577-1581.

Bose, Bikash, et al., "Neurophysiologic Monitoring of Spinal Nerve Root Function During Instrumented Posterior Lumbar Spine Surgery", Spine, 27(13), (2002), 1444-1450.

Calancie, Blair et al. "Stimulus-evoked EMG Monitoring During Transpedicular Lumbrosacral Spine Instrumentation: Initial Clinical Results". 1994. Spine. vol. 19, No. 24, pp. 2780-2786.

Clements, David, et al., "Evoked and Spontaneous Electromyography to Evaluate Lumbosacral Pedicle Screw Placement", Spine, 21(5), (1996), 600-604.

Danesh-Clough, T., et al., "The use of evoked EMG in detecting misplaced thoracolumbar pedicle screws", Spine. 26(12), Orthopaedic Department, Dunedin Hospital, (Jun. 15, 2001), 1313-1316.

Darden, B. V., et al., "A comparison of impedance and electromyogram measurements in detecting the presence of pedicle wall breakthrough", Spine. 23(2), Charlotte Spine Center, North Carolina, (Jan. 15, 1998), 256-262.

Ebraheim, N. A., "Anatomic relations between the lumbar pedicle and the adjacent neural structures", Spine. 22(20), Department of Orthopaedic Surgery, Medical College of Ohio, (Oct. 15, 1997), 2338-2341.

Ford, Douglas, et al., "Electrical Characteristics of Peripheral Nerve Stimulators Implications for Nerve Localization", Regional Anesthesia, 9, (1984), 73-77.

Glassman, Steven, et al., "A Prospective Analysis of Intraoperative Electromyographic Monitoring of Pedicle Screw Placement With Computed Tomographic Scan Confirmation", Spine , 20(12), (1995), 1375-1379.

Greenblatt, Gordon, et al., "Needle Nerve Stimulator-Locator: Nerve Blocks with a New Instrument for Locating Nerves", Anesthesia & Analgesia, 41(5), (1962), 599-602.

Haig, "Point of View", Spine 27 (24), 2819.

Haig, A. J., et al., "The relation among spinal geometry on MRI, paraspinal electromyographic abnormalities, and age in persons referred for electrodiagnostic testing of low back symptoms", Spine. 27(17), Department of Physical Medicine and Rehabilitation, University of Michigan, (Sep. 1, 2002), 1918-1925.

Holland, N. R., et al., "Higher electrical stimulus intensities are required to activate chronically compressed nerve roots. Implications for intraoperative electromyographic pedicle screw testing", Spine. 23(2), Department of Neurology, John Hopkins University School of Medicine, (Jan. 15, 1998), 224-227.

Holland, Neil, "Intraoperative Electromyography During Thoracolumbar Spinal Surgery", Spine, 23(17), (1998), 1915-1922.

Journee et al., "System for Intra-Operative Monitoring of the Cortical Integrity of the Pedicle During Pedicle Screw Placement in Low-Back Surgery: Design and Clinical Results," Sensory and Neuromuscular Diagnostic Instrumentation and Data Analysis I, 18th Annual International Conference on Engineering in Medicine and Biology Society, Amsterdam, 1996, pp. 144-145.

Lenke, Lawrence, et al., "Triggered Electromyographic Threshold for Accuracy of Pedicle Screw Placement", Spine, 20 (14), (1995), 1585-1591.

Maguire, J., et al., "Evaluation of Intrapedicular Screw Position Using Intraoperative Evoked Electromyography", Spine, 20(9), (1995), 1 068-1074.

Martin, David , et al., "Initiation of Erection and Semen Release by Rectal Probe Electrostimulation (RPE)", the Williams & Wilkins Co., (1983), 637-642.

Minahan, R. E., et al., "The effect of neuromuscular blockade on pedicle screw stimulation thresholds", Spine. 25(19), Department of Neurology, Johns Hopkins University, School of Medicine, (Oct. 1, 2000), 2526-2530.

Moed et al., "Insertion of an iliosacral implant in an animal model," Journal of Bone and Joint Surgery, 1999, 81A(11): 1529-1537.

Moed et al., "Intraoperative monitoring with stimulus-evoked electromyography during placement of iliosacral screws," the Journal of Bone and Joint Surgery, 1998, 81A(4): 10 pages.

Pither, Charles, et al., "The Use of Peripheral Nerve Stimulators for Regional Anesthesia: Review of Experimental Characteristics, Technique, and Clinical Applications", Regional Anesthesia, (1985), 10:47-53.

Raj, P, et al., "Infraclavicular Brachial Plexus Block—A New Approach", Anesthesia and Analgesia, (52)6, (1973), 897-904.

Raj, P., et al., "The Use of Peripheral Nerve Stimulators for Regional Anesthesia", Clinical Issues in Regional Anesthesia, 1 (4), (1985), 1-6.

Raj, P., et al., "Use of the nerve Stimulator of Peripheral Blocks", Regional Anesthesia, (Apr.-Jun. 1980), 14-21.

Raymond, Stephen, et al., "The Nerve Seeker: A System for Automated Nerve Localization", Regional Anesthesia, 17(3), (1992), 151-162.

Shafik, Ahmed, "Cavernous Nerve Simulation through an Extrapelvic Subpubic Approach: Role in Pencil Erection", Eur. Urol, 26, (1994), 98-102.

Toleikis, J., et al., "The Usefulness of Electrical Stimulation for Assessing Pedicle Screw Replacements", Journal of Spinal Disorder, 13(4), (2000), 283-289.

* cited by examiner

SYSTEM FOR DETERMINING NERVE DIRECTION TO A SURGICAL INSTRUMENT

CROSS-REFERENCES TO RELATED APPLICATIONS

This application is a continuation of U.S. patent application Ser. No. 13/427,760 filed Mar. 22, 2012, which is a continuation of U.S. patent application Ser. No. 11/182,545 filed Jul. 15, 2005 (now U.S. Pat. No. 8,147,421), which is a continuation of International Application No. PCT/US03/02056 filed Jan. 15, 2003 and published on Aug. 5, 2004 as International Publication No. WO 2004/064634.

BACKGROUND

Systems and methods exist for monitoring nerves and nerve muscles. One such system determines when a needle is approaching a nerve. The system applies a current to the needle to evoke a muscular response. The muscular response is visually monitored, typically as a shake or "twitch." When such a muscular response is observed by the user, the needle is considered to be near the nerve coupled to the responsive muscle. These systems require the user to observe the muscular response (to determine that the needle has approached the nerve). This may be difficult depending on the competing tasks of the user. In addition, when general anesthesia is used during a procedure, muscular response may be suppressed, limiting the ability of a user to detect the response.

While generally effective (although crude) in determining nerve proximity, such existing systems are incapable of determining the direction of the nerve to the needle or instrument passing through tissue or passing by the nerves. While the surgeon may appreciate that a nerve is in the general proximity of the instrument, the inability to determine the direction of the nerve relative to the instrument can lead to guess work by the surgeon in advancing the instrument, which raises the specter of inadvertent contact with, and possible damage to, the nerve.

SUMMARY

The present application may be directed to at least reduce the effects of the above-described problems with the prior art. The present application includes a system and related methods for determining the direction of a surgical instrument to a nerve during surgical procedures. According to one aspect of the system, this involves the use of neurophysiology-based monitoring to determine nerve direction to surgical instruments employed in accessing a surgical target site. The system may do so in an automated, easy to use, and easy to interpret fashion so as to provide a surgeon-driven system.

The system may combine neurophysiology monitoring with any of a variety of instruments used in or in accessing a surgical target site (referred to herein as "surgical access instruments"). By way of example only, such surgical access instruments may include, but are not necessarily limited to, any number of devices or components for creating an operative corridor to a surgical target site, such as K-wires, sequentially dilating cannula systems, distractor systems, and/or retractor systems. Although described herein largely in terms of use in spinal surgery, it is to be readily appreciated that the teachings of the methods and systems may be suitable for use in any number of additional surgical procedures where tissue having significant neural structures must be passed through (or near) in order to establish an operative corridor to a surgical target site.

A general method according to the present application may include: (a) providing multiple (e.g., four orthogonally-disposed) electrodes around the periphery of the surgical access instrument; (b) stimulating the electrodes to identify the current threshold ($I_{Thresh}$) necessary to innervate the muscle myotome coupled to the nerve near the surgical access instrument; (c) determining the direction of the nerve relative to the surgical access instrument via successive approximation; and (d) communicating this successive approximation direction information to the surgeon in an easy-to-interpret fashion.

The act of providing multiple (e.g., four orthogonally-disposed) electrodes around the periphery of the surgical access instrument may be accomplished in any number of suitable fashions depending upon the surgical access instrument in question. For example, the electrodes may be disposed orthogonally on any or all components of a sequential dilation system (including an initial dilator, dilating cannulae, and working cannula), as well as speculum-type and/or retractor-based access systems. The act of stimulating may be accomplished by applying any of a variety of suitable stimulation signals to the electrode(s) on the surgical accessory, including voltage and/or current pulses of varying magnitude and/or frequency. The stimulating act may be performed during and/or after the process of creating an operative corridor to the surgical target site.

The act of determining the direction of the surgical access instrument relative to the nerve via successive approximation is preferably performed by monitoring or measuring the EMG responses of muscle groups associated with a particular nerve and innervated by the nerve(s) stimulated during the process of gaining surgical access to a desired surgical target site.

The act of communicating this successive approximation information to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example only, this may include providing an arc or other graphical representation that indicates the general direction to the nerve. The direction indicator may quickly start off relatively wide, become successively more narrow (based on improved accuracy over time), and may conclude with a single arrow designating the relative direction to the nerve.

Communicating this successive approximation information may be an important feature. By providing such direction information, a user will be kept informed as to whether a nerve is too close to a given surgical accessory element during and/or after the operative corridor is established to the surgical target site. This is particularly advantageous during the process of accessing the surgical target site in that it allows the user to actively avoid nerves and redirect the surgical access components to successfully create the operative corridor without impinging or otherwise compromising the nerves.

Based on this nerve direction feature, an instrument is capable of passing through virtually any tissue with minimal (if any) risk of impinging or otherwise damaging associated neural structures within the tissue, thereby making the system suitable for a wide variety of surgical applications.

A direction-finding algorithm that finds a stimulation threshold current one electrode at a time for a plurality of electrodes (e.g., four electrodes) may require 40 to 80 stimulations in order to conclude with a direction vector. At a stimulation rate of 10 Hz, this method may take four to eight seconds before any direction information is available to a surgeon. A surgeon may grow impatient with the system. An "arc" method described herein may improve the direction-finding algorithm and provide nerve direction information to the surgeon sooner. The system may display direction to the nerve during a sequence of stimulations as an "arc" (or wedge), which represents a zone containing the nerve. Computation of the direction arc (wedge) may be based on stimulation current threshold ranges, instead of precise, finally-calculated stimulation current threshold levels. Display of the direction arc (wedge) is possible at any time that the stimulation current thresholds are known to fall within a range of values.

One aspect relates to a system comprising: a surgical accessory having at least one stimulation electrode; and a control unit capable of electrically stimulating at least one stimulation electrode on said surgical accessory, sensing a response of a nerve depolarized by said stimulation, determining a direction from the surgical accessory to the nerve based upon the sensed response, and communicating said direction to a user. The system may further comprise an electrode configured to sense a neuromuscular response of a muscle coupled to said depolarized nerve. The electrode may be operable to send the response to the control unit.

The surgical accessory may comprise a system for establishing an operative corridor to a surgical target site. The system for establishing an operative corridor may comprise a series of sequential dilation cannulae, where at least one cannula has said at least one stimulation electrode near a distal end. The system for establishing an operative corridor may further comprise a K-wire. The K-wire may have a first stimulation electrode at a distal tip. The K-wire may have a second stimulation electrode away from the distal tip. The K-wire may be slidably received in the surgical accessory, where the surgical accessory has a plurality of electrodes. The system for establishing an operative corridor may be configured to access a spinal target site. The system for establishing an operative corridor may be configured to establish an operative corridor via a lateral, trans-psoas approach.

The system may further comprise a handle coupled to the surgical accessory. The handle may have at least one button for initiating the electrical stimulation from the control unit to at least one stimulation electrode on the surgical accessory.

The control unit may comprise a display operable to display an electromyographic (EMG) response of the muscle. The control unit may comprise a touch-screen display operable to receive commands from a user.

The surgical accessory may comprise a plurality of stimulation electrodes. The stimulation electrodes may be positioned near a distal end of the surgical accessory. The stimulation electrodes may be positioned in a two-dimensional plane. The stimulation electrodes may be positioned orthogonally to form a cross. The control unit may derive x and y Cartesian coordinates of a nerve direction with respect to the surgical accessory by using $x = i_w^2 - i_e^2$ and $y = i_s^2 - i_n^2$ where $i_e$, $i_w$, $i_n$, and $i_s$ represent stimulation current thresholds for east, west, north, and south electrodes. The stimulation electrodes may comprise a first set of electrodes in a first two-dimensional plane and a second set of at least one electrode in another plane that is parallel to the first plane. The stimulation electrodes may form a tetrahedron. The control unit may be configured to determine a three-dimensional vector from a reference point on the surgical accessory to a nerve.

The control unit may determine a three-dimensional vector from a reference point on the surgical accessory to a nerve by using:

$$x = \frac{1}{4R}(d_w^2 - d_e^2)$$

$$y = \frac{1}{4R}(d_s^2 - d_n^2) \text{ and } z = \frac{1}{4D}(d_o^2 - d_k^2).$$

The control unit may be configured to determine a three-dimensional vector from a reference point on the surgical accessory to a nerve by using:

$$x = \frac{1}{4RK}(i_w - i_e)$$

$$y = \frac{1}{4RK}(i_s - i_n) \text{ and } z = \frac{1}{4DK}(i_c - i_k)$$

where $i_x$ is a stimulation current threshold of a corresponding stimulation electrode (west, east, south or north), $i_k$ is the stimulation current threshold of a k-wire electrode, $i_s$ is calculated from: $i_c + KR^2 = \frac{1}{4}(i_w + i_e + i_s + i_n)$. The control unit may be further configured to display the three-dimensional vector to a user.

The stimulation electrodes may comprise two pairs of electrodes. The stimulation electrodes may comprise a first electrode at a first longitudinal level of the surgical accessory and a second electrode at a second longitudinal level of the surgical accessory.

The control unit may be configured to electrically stimulate a first stimulation electrode with a first current signal, determine whether a first stimulation current threshold has been bracketed, stimulate a second stimulation electrode with a second current signal, and determine whether a second stimulation current threshold has been bracketed. The first and second current signals may be equal. The control unit may be further configured to determine a first range for the first stimulation current threshold, and determine a second range for the second stimulation current threshold. Each range may have a maximum stimulation current threshold value and a minimum stimulation current threshold value. The control unit may be configured to process the first and second ranges by using $x_{min} = i_{w,min}^2 - i_{e,max}^2$; $x_{max} = i_{w,max}^2 - i_{e,min}^2$; $y_{min} = i_{s,min}^2 - i_{n,max}^2$; $y_{max} = i_{s,max}^2 - i_{n,min}^2$, where $i_e$, $i_w$, $i_n$, and $i_s$ represent stimulation current thresholds for east, west, north, and south electrodes. The control unit may be configured to process the first and second ranges by using $$x_{min} = \frac{1}{4R}(d_{w,min}^2 - d_{e,max}^2),$$

$$x_{max} = \frac{1}{4R}(d_{w,max}^2 - d_{e,min}^2)$$

$$y_{min} = \frac{1}{4R}(d_{s,min}^2 - d_{n,max}^2),$$

$$y_{max} = \frac{1}{4R}(d_{s,max}^2 - d_{n,min}^2)$$

where d is a distance from a nerve to east, west, north, and south electrodes.

The control unit may be configured to process the first and second ranges and display an arc indicating a general direction of a nerve from the surgical accessory. The control unit may be further configured to electrically stimulate the first stimulation electrode with a third current signal, determine whether the first stimulation current threshold has been bracketed, stimulate the second stimulation electrode with a fourth current signal, and determine whether the second stimulation current threshold has been bracketed.

The control unit may be configured to electrically stimulate each electrode until a stimulation current threshold has been bracketed. The control unit may be configured to display an arc indicating a general direction of a nerve from the surgical accessory and narrow the arc as stimulation current thresholds are bracketed. The control unit may be further configured to electrically stimulate the first and second stimulation electrodes to bisect each bracket until a first stimulation current threshold has been found for the first stimulation electrode and a second stimulation current threshold has been found for the second stimulation electrode within a predetermined range of accuracy. The control unit may be configured to display an arc indicating a general direction of a nerve from the surgical accessory and narrow the arc as stimulation current threshold brackets are bisected.

The control unit may be configured to emit a sound when the control unit determines a distance between the surgical accessory and the nerve has reached a predetermined level. The control unit may be configured to emit a sound that indicates a distance between the surgical accessory and the nerve. The surgical accessory may be dimensioned to be inserted percutaneously through a hole to a surgical site.

Another aspect relates to a surgical instrument comprising an elongated body and a plurality of electrodes on the elongated body. Each electrode is configured to produce electrical current pulses at a plurality of current levels. At least one current level being sufficient to depolarize a nerve when the elongated body is near the nerve. The elongated body may comprise a K-wire. The elongated body may comprise a cannula. The electrodes may comprise four orthogonal electrodes in a two-dimensional plane. The electrodes may comprise a first set of electrodes in a first two-dimensional plane and a second set of at least one electrode in another plane that is parallel to the first plane. The electrodes may be configured to produce electrical current pulses round-robin at a first current level, then produce electrical current pulses round-robin at a second current level. The elongated body may comprise a sequential dilation system.

Another aspect relates to a processing unit operable to determine ranges of nerve-stimulation threshold current levels for a plurality of electrodes on a surgical instrument inserted into a body.

Another aspect relates to a method comprising providing a system operable to determine a direction of a nerve from a surgical instrument inserted in a body; and installing software in the system. The method may further comprise configuring a minimum threshold peak-to-peak voltage level of a neuromuscular response.

Another aspect relates to a method of finding a direction of a nerve from a surgical instrument. The method comprises: electrically stimulating a first stimulation electrode on a surgical instrument inserted in a body with a first current signal; determining whether a first stimulation current threshold has been bracketed by the first stimulation current signal; electrically stimulating a second stimulation electrode on the surgical instrument with a second current signal; and determining whether a second stimulation current threshold has been bracketed by the second stimulation current signal.

The first and second current signals may be equal. The method may further comprise determining a first range for the first stimulation current threshold, and determining a second range for the second stimulation current threshold, each range having a maximum stimulation current threshold value and a minimum stimulation current threshold value. The method may further comprise processing the first and second ranges and displaying an arc indicating a general direction of a nerve from the surgical accessory.

The method may further comprise electrically stimulating the first stimulation electrode with a third current signal; determining whether the first stimulation current threshold has been bracketed; stimulating the second stimulation electrode with a fourth current signal; and determining whether the second stimulation current threshold has been bracketed. The method may further comprise electrically stimulating each electrode until a stimulation current threshold has been bracketed. The method may further comprise displaying an arc indicating a general direction of a nerve from the surgical accessory and narrowing the arc as stimulation current thresholds are bracketed.

The method may further comprise electrically stimulating the first and second stimulation electrodes to bisect each bracket until a first stimulation current threshold has been found for the first stimulation electrode and a second stimulation current threshold has been found for the second stimulation electrode within a predetermined range of accuracy. The method may further comprise displaying an arc indicating a general direction of a nerve from the surgical accessory and narrow the arc as stimulation current threshold brackets are bisected.

DETAILED DESCRIPTION

Illustrative embodiments of the application are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
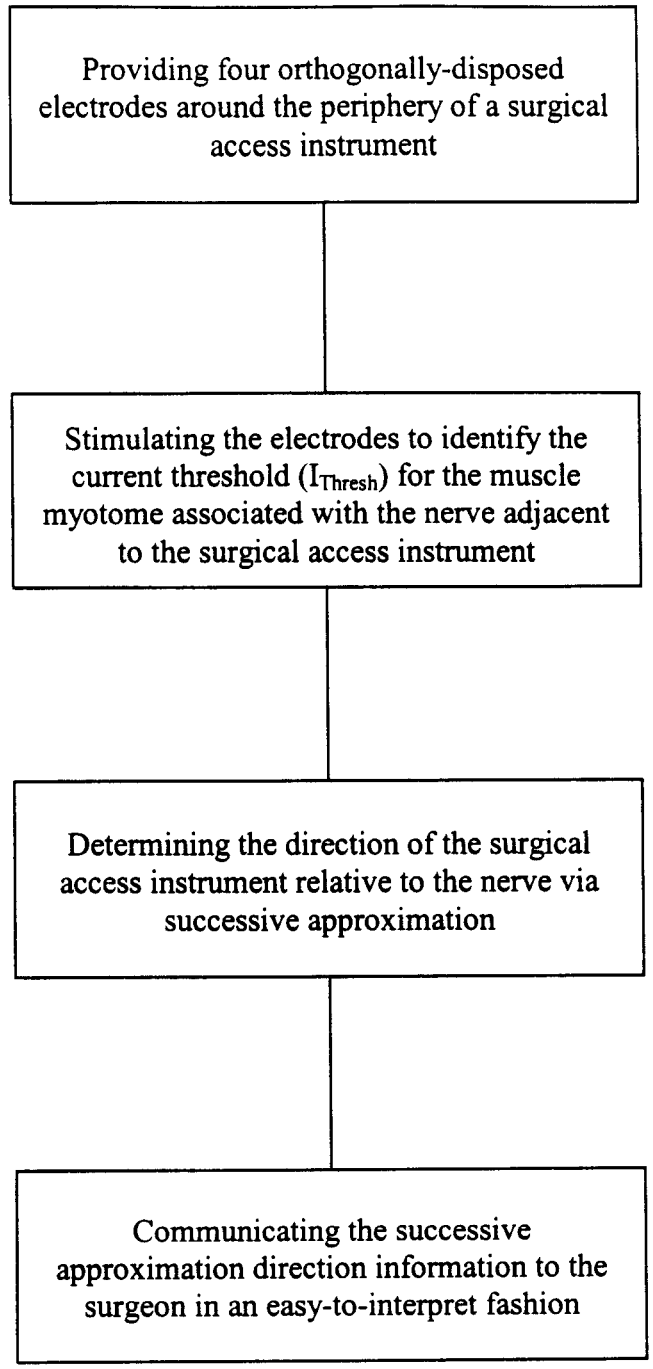
FIG. 1 is a flow chart illustrating fundamental functions of a neurophysiology-based surgical system according to one embodiment of the present application.

FIG. 1 illustrates general functions according to one embodiment of the present application, namely: (a) providing multiple (e.g., four orthogonally-disposed) electrodes around the periphery of the surgical access instrument; (b) stimulating the electrodes to identify the current threshold ($I_{Thresh}$) necessary to innervate the muscle myotome coupled to the nerve near the surgical access instrument; (c) determining the direction of the nerve relative to the surgical access instrument via successive approximation; and (d) communicating this successive approximation direction information to the surgeon in an easy-to-interpret fashion.

The act of providing multiple (e.g., four orthogonally-disposed) electrodes around the periphery of the surgical access instrument may be accomplished in any number of suitable fashions depending upon the surgical access instrument in question. For example, the electrodes may be disposed orthogonally on any or all components of a sequential dilation system (including an initial dilator, dilating cannulae, and working cannula), as well as speculum-type and/or retractor-based access systems, as disclosed in the co-pending, co-assigned May, 2002 U.S. Provisional application incorporated above. The act of stimulating may be accomplished by applying any of a variety of suitable stimulation signals to the electrode(s) on the surgical accessory, including voltage and/or current pulses of varying magnitude and/or frequency. The stimulating act may be performed during and/or after the process of creating an operative corridor to the surgical target site.

The act of determining the direction of the surgical access instrument relative to the nerve via successive approximation is preferably performed by monitoring or measuring the EMG responses of muscle groups associated with a particular nerve and innervated by the nerve(s) stimulated during the process of gaining surgical access to a desired surgical target site.

The act of communicating this successive approximation information to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example only, this may include providing an arc or other graphical representation that indicates the general direction to the nerve. The direction indicator may quickly start off relatively wide, become successively more narrow (based on improved accuracy over time), and may conclude with a single arrow designating the relative direction to the nerve.

The direction indicator may be an important feature. By providing such direction information, a user will be kept informed as to whether a nerve is too close to a given surgical accessory element during and/or after the operative corridor is established to the surgical target site. This is particularly advantageous during the process of accessing the surgical target site in that it allows the user to actively avoid nerves and redirect the surgical access components to successfully create the operative corridor without impinging or otherwise compromising the nerves.

Based on this nerve direction feature, then, an instrument is capable of passing through virtually any tissue with minimal (if any) risk of impinging or otherwise damaging associated neural structures within the tissue, thereby making the system suitable for a wide variety of surgical applications.

Figure 2:
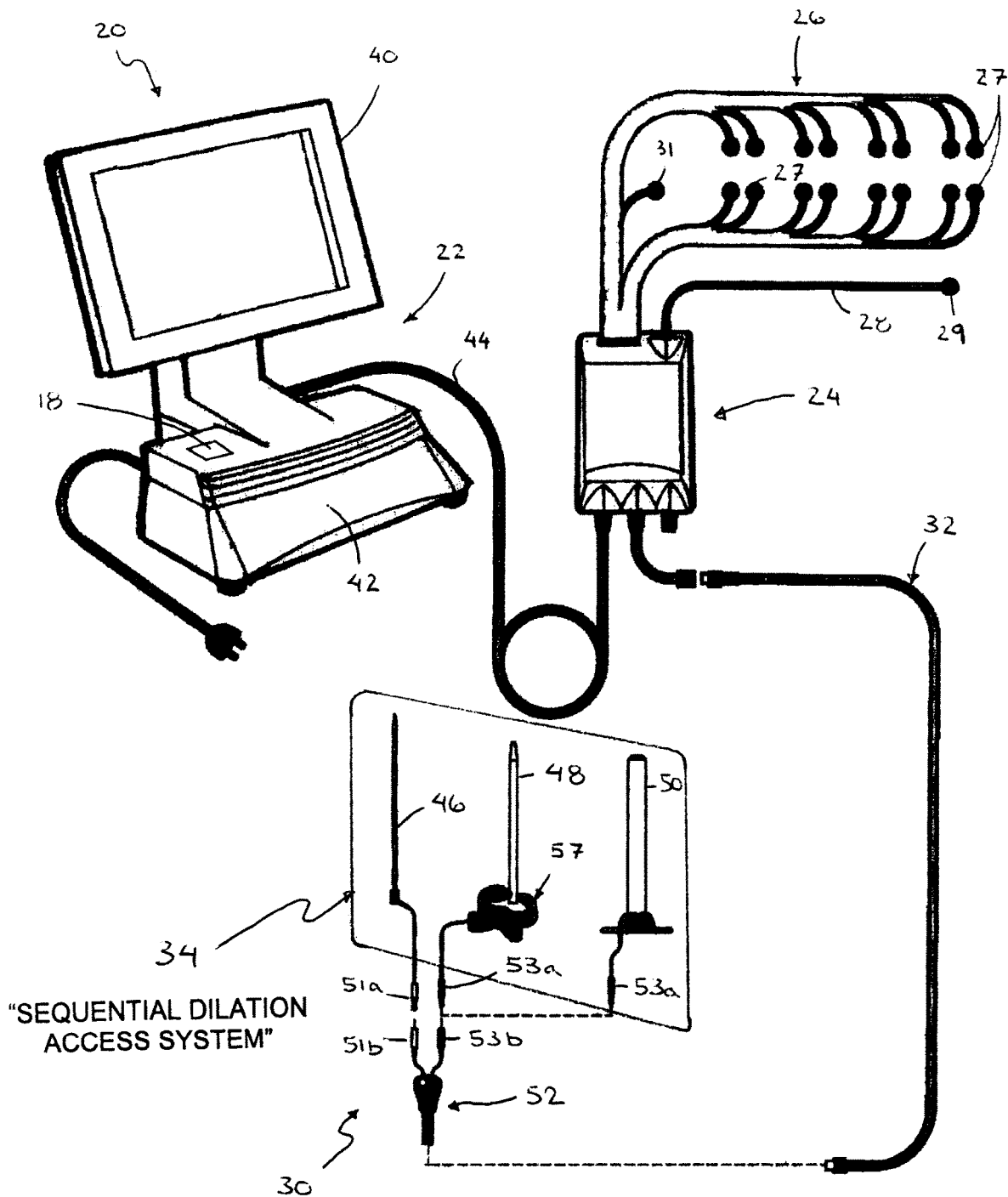
FIG. 2 is a perspective view of an exemplary surgical system capable of performing the functions in FIG. 1 and determining nerve direction to surgical instruments employed in accessing a surgical target site.
Figure 3:
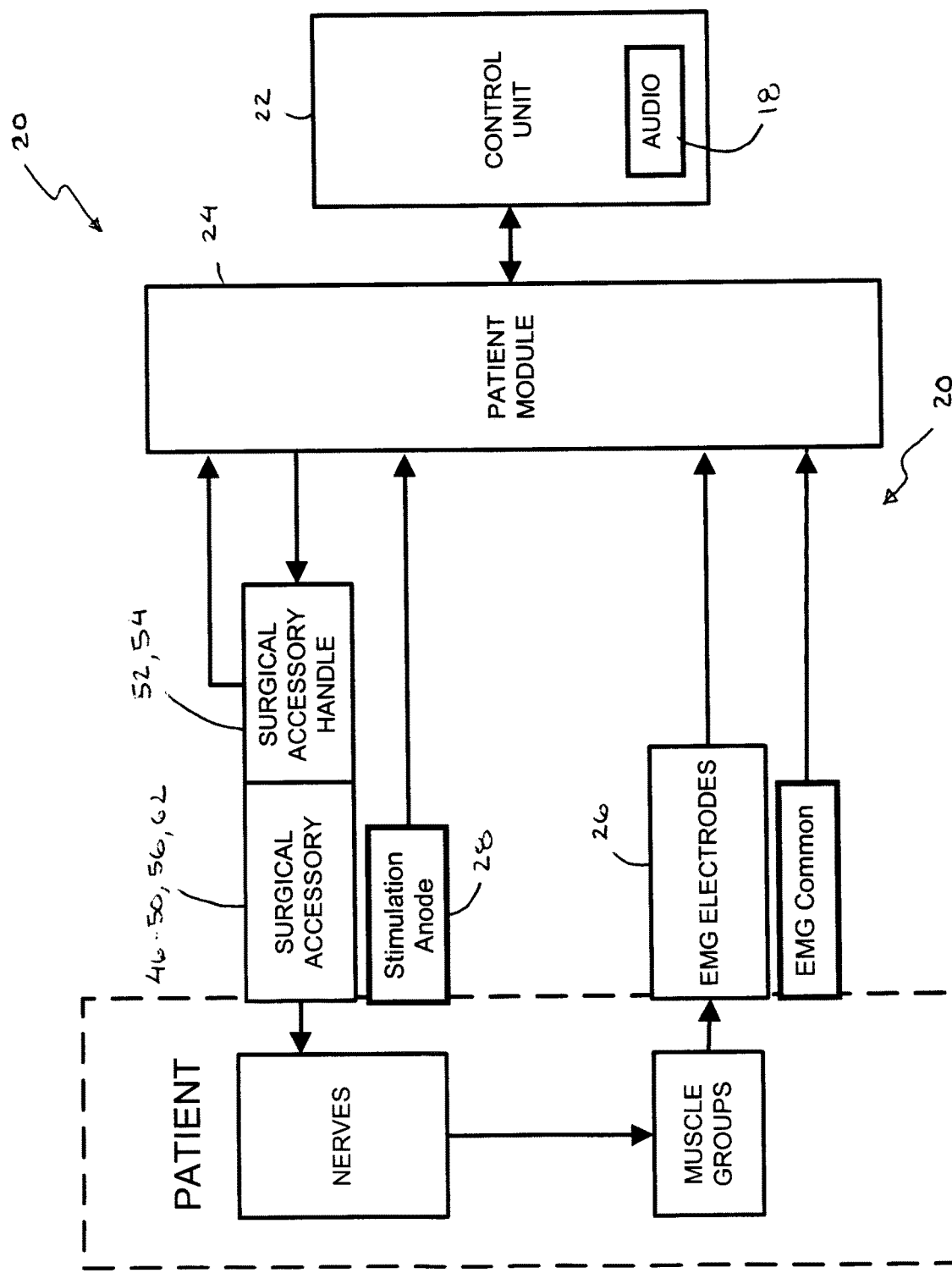
FIG. 3 is a block diagram of the surgical system shown in FIG. 2.

FIGS. 2-3 illustrate, by way of example only, a surgical system 20 provided in accordance with a broad aspect of the present application. The surgical system 20 includes a control unit 22, a patient module 24, an EMG harness 26 and return electrode 28 coupled to the patient module 24, and (by way of example only) a sequential dilation surgical access system 34 capable of being coupled to the patient module 24 via cable 32. The sequential dilation access system 34 comprises, by way of example only, a K-wire 46, one or more dilating cannula 48, and a working cannula 50.

The control unit 22 includes a touch screen display 40 and a base 42, which collectively contain the essential processing capabilities (software and/or hardware) for controlling the surgical system 20. The control unit 22 may include an audio unit 18 that emits sounds according to a location of a surgical element with respect to a nerve, as described herein.

The patient module 24 is connected to the control unit 22 via a data cable 44, which establishes the electrical connections and communications (digital and/or analog) between the control unit 22 and patient module 24. The main functions of the control unit 22 include receiving user commands via the touch screen display 40, activating stimulation electrodes on the surgical access instruments 30, processing signal data according to defined algorithms (described below), displaying received parameters and processed data, and monitoring system status and report fault conditions. The touch screen display 40 is preferably equipped with a graphical user interface (GUI) capable of communicating information to the user and receiving instructions from the user. The display 40 and/or base 42 may contain patient module interface circuitry (hardware and/or software) that commands the stimulation sources, receives digitized signals and other information from the patient module 24, processes the EMG responses to extract characteristic information for each muscle group, and displays the processed data to the operator via the display 40.

In one embodiment, the surgical system 20 is capable of determining nerve direction relative to each K-wire 46, dilation cannula 48 and/or the working cannula 50 during and/or following the creation of an operative corridor to a surgical target site. Surgical system 20 accomplishes this by having the control unit 22 and patient module 24 cooperate to send electrical stimulation signals to each of the orthogonally-disposed stimulation electrodes 1402A-1402D (FIGS. 14A-14B) on the various surgical access instruments 46-50 (e.g., electrodes on the distal ends of the instruments 46-50). Depending upon the location of the surgical access instruments 46-50 within a patient, the stimulation signals may cause nerves adjacent to or in the general proximity of the surgical instruments 46-50 to depolarize. This causes muscle groups to innervate and generate EMG responses, which can be sensed via the EMG harness 26. The nerve direction feature of the system 20 is based on assessing the evoked response of the various muscle myotomes monitored by the surgical system 20 via the EMG harness 26.

The sequential dilation surgical access system 34 is designed to bluntly dissect the tissue between the patient's skin and the surgical target site. Each K-wire 46, dilating cannula 48 and/or working cannula 50 may be equipped with multiple (e.g., four orthogonally-disposed) stimulation electrodes to detect the location of nerves in between the skin of the patient and the surgical target site. To facilitate this, a surgical hand-piece 52 is provided for electrically coupling the surgical accessories 46-50 to the patient module 24 (via cable 32). In a preferred embodiment, the surgical hand piece 52 includes one or more buttons for selectively initiating the stimulation signal (preferably, a current signal) from the control unit 22 to a particular surgical access instrument 46-50. Stimulating the electrode(s) on these surgical access instruments 46-50 during passage through tissue in forming the operative corridor will cause nerves that come into close or relative proximity to the surgical access instruments 46-50 to depolarize, producing a response in the innervated myotome.

By monitoring the myotomes associated with the nerves (via the EMG harness 26 and recording electrode 27) and assessing the resulting EMG responses (via the control unit 22), the sequential dilation access system 34 is capable of detecting the direction to such nerves. Direction determination provides the ability to actively negotiate around or past such nerves to safely and reproducibly form the operative corridor to a particular surgical target site. In one embodiment, by way of example only, the sequential dilation access system 34 is particularly suited for establishing an operative corridor to an intervertebral target site in a postero-lateral, trans-psoas fashion so as to avoid the bony posterior elements of the spinal column.

A discussion of the algorithms and principles behind the neurophysiology for accomplishing these functions will now be undertaken, followed by a detailed description of the various implementations of these principles.

Figure 4:
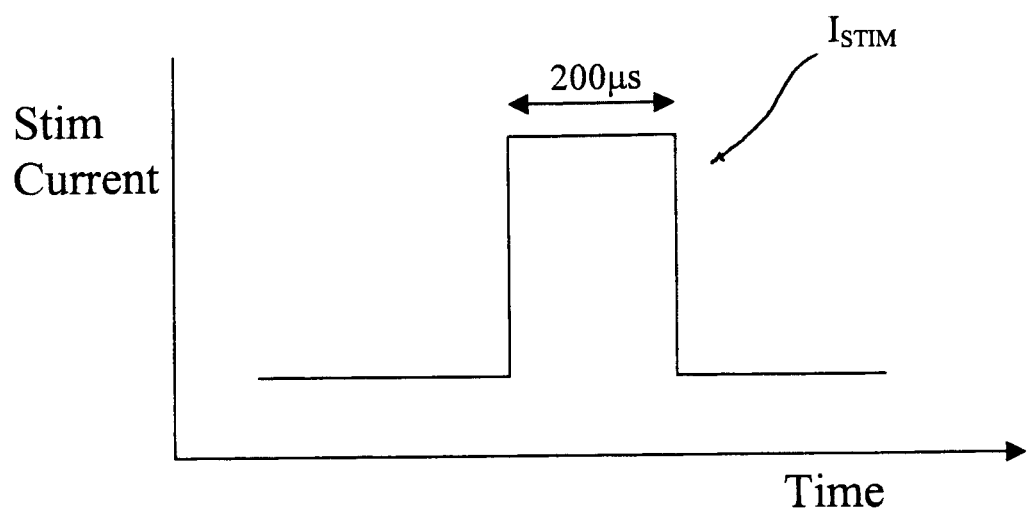
FIG. 4 is a graph illustrating a plot of a stimulation current pulse capable of producing a neuromuscular response (EMG) of the type shown in FIG. 5.
Figure 5:
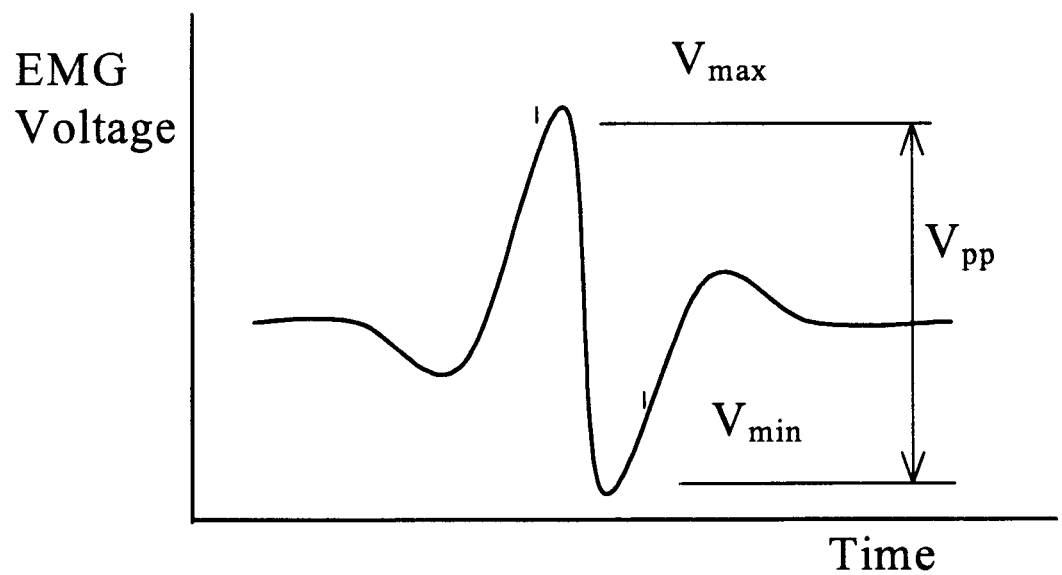
FIG. 5 is a graph illustrating a plot of the neuromuscular response (EMG) of a given myotome over time based on a current stimulation pulse (such as shown in FIG. 4) applied to a nerve bundle coupled to the given myotome.

FIGS. 4 and 5 illustrate a fundamental aspect of the present application: a stimulation signal (FIG. 4) and a resulting evoked response (FIG. 5). By way of example only, the stimulation signal is preferably a stimulation current signal ($I_{Stim}$) having rectangular monophasic pulses with a frequency and amplitude adjustable by system software. In one embodiment, the stimulation current ($I_{Stim}$) may be coupled in any suitable fashion (i.e., AC or DC) and comprises rectangular monophasic pulses of 200 microsecond duration. The amplitude of the current pulses may be fixed, but may preferably sweep from current amplitudes of any suitable range, such as from 2 to 100 mA. For each nerve and myotome there is a characteristic delay from the stimulation current pulse to the EMG response (typically between 5 to 20 ms). To account for this, the frequency of the current pulses may be set at a suitable level, such as, in a preferred embodiment, 4 Hz to 10 Hz (and most preferably 4.5 Hz), so as to prevent stimulating the nerve before it has a chance to recover from depolarization. The EMG response shown in FIG. 5 can be characterized by a peak-to-peak voltage of $V_{pp}=V_{max}-V_{min}$.

Figure 6:
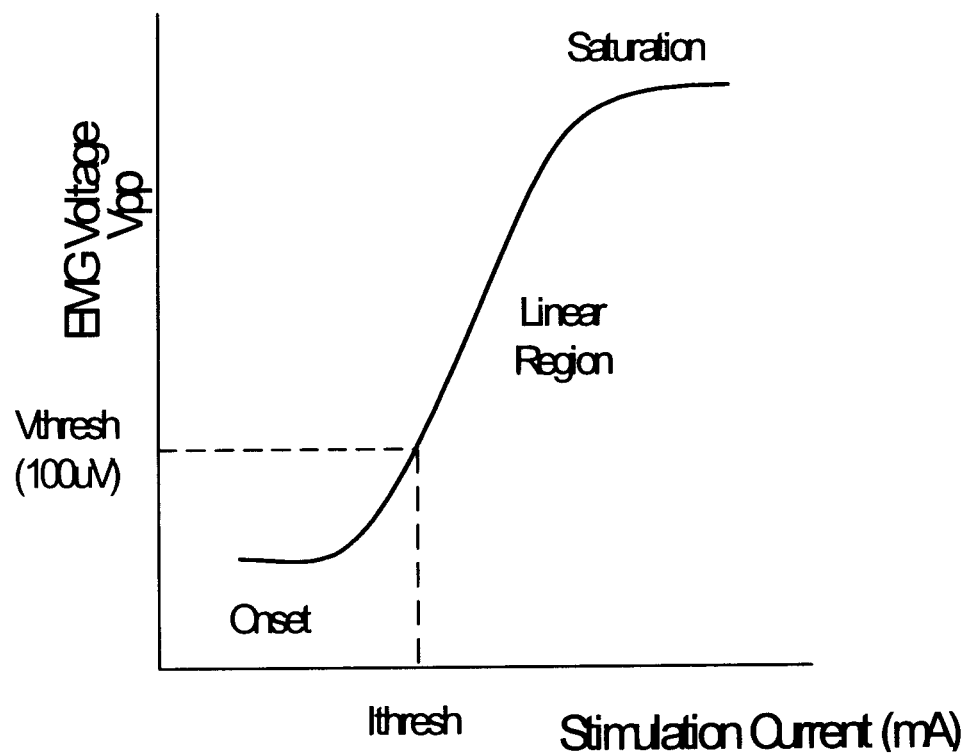
FIG. 6 is a graph illustrating a plot of EMG response peak-to-peak voltage (Vpp) for each given stimulation current level ($I_{Stim}$) forming a stimulation current pulse (otherwise known as a "recruitment curve") for the system of FIG. 2.
Figure 7A:
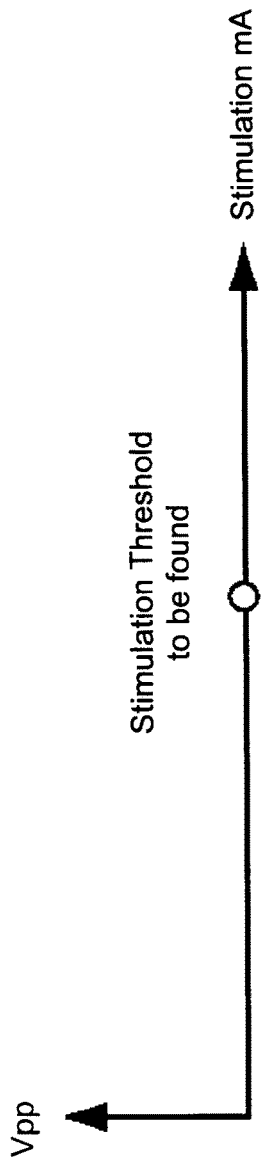
FIG. 7A-7E are graphs illustrating a current threshold-hunting algorithm that may be used by the system of FIG. 2.
Figure 7B:
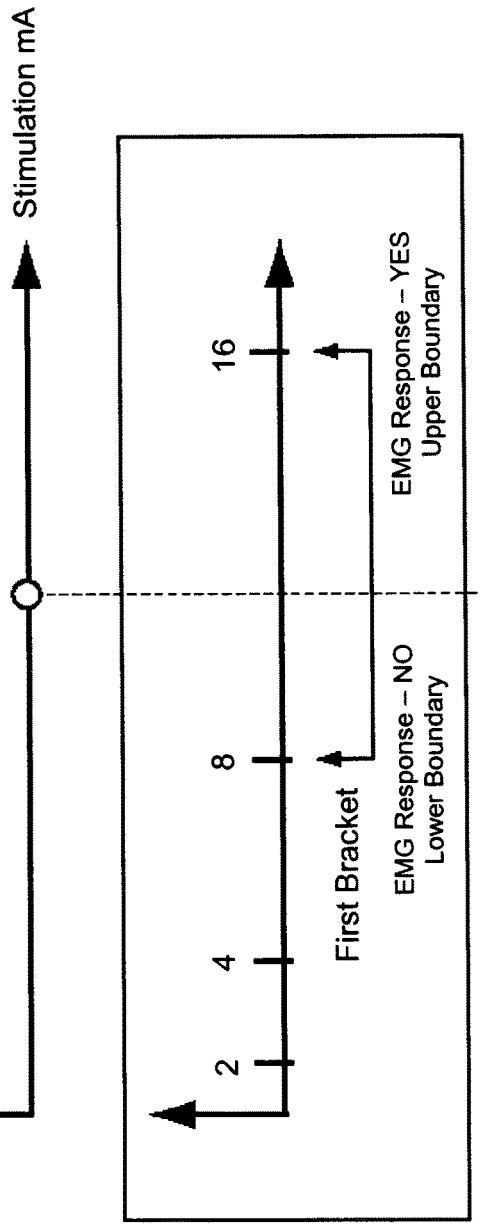
Figure 7C:
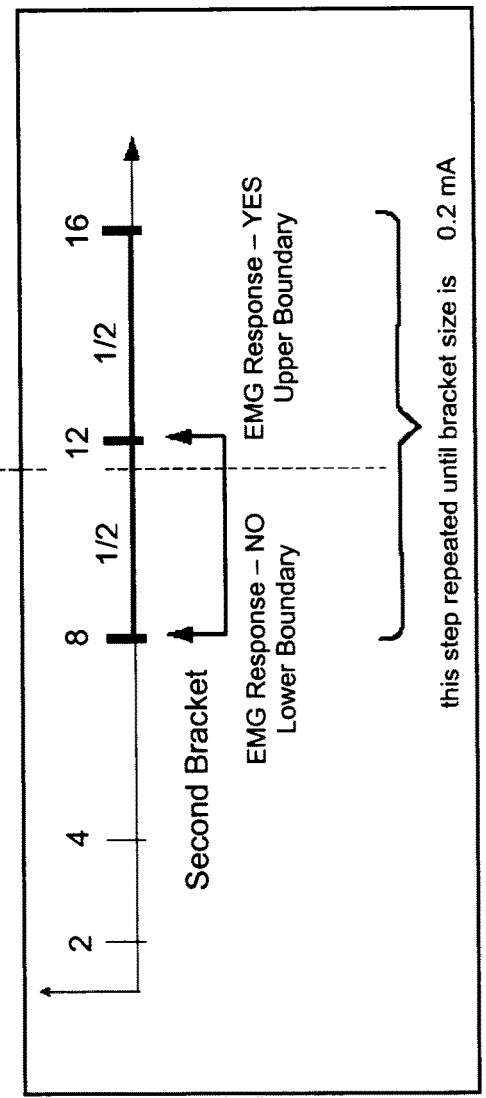
Figures 7D, 7E:
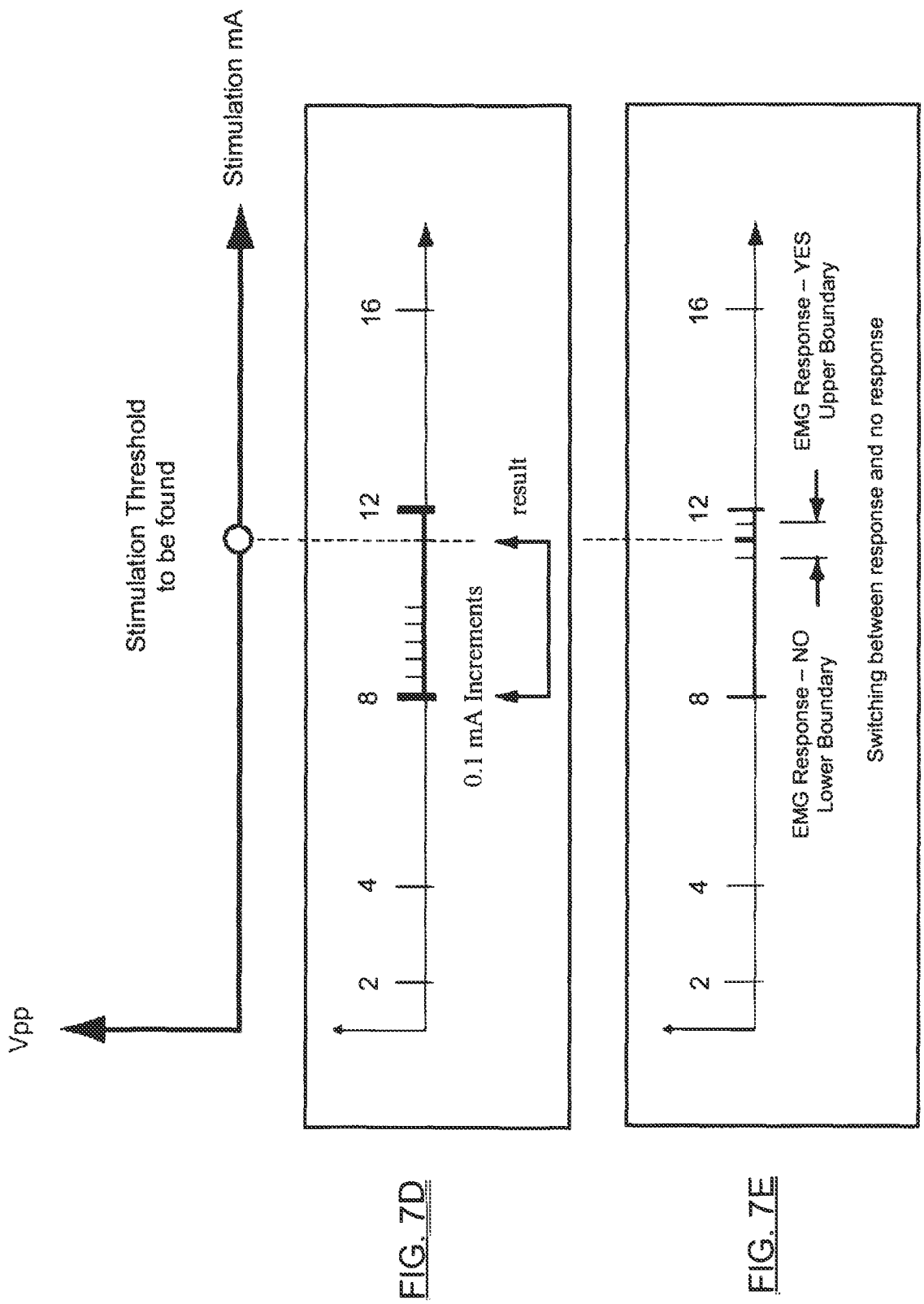

A basic premise behind the neurophysiology employed by the system 20 is that each nerve has a characteristic threshold current level ($I_{Thresh}$) at which it will depolarize. Below this threshold, current stimulation will not evoke a significant EMG response ($V_{pp}$). Once the stimulation threshold ($I_{Thresh}$) is reached, the evoked response is reproducible and increases with increasing stimulation until saturation is reached. This relationship between stimulation current and EMG response may be represented graphically via a so-called "recruitment curve," such as shown in FIG. 6, which includes an onset region, a linear region, and a saturation region. By way of example only, the system 20 may define a significant EMG response to have a Vpp of approximately 100 uV. In a preferred embodiment, the lowest stimulation current that evokes this threshold voltage ($V_{thresh}$) is called a stimulation current threshold or "$I_{Thresh}$."

In order to obtain this useful information, the system 20 should first identify the peak-to-peak voltage (Vpp) of each EMG response that corresponds to a given stimulation current ($I_{Stim}$). The existence of stimulation and/or noise artifacts, however, can conspire to create an erroneous Vpp measurement of the electrically evoked EMG response. To overcome this challenge, the surgical system 20 may employ any number of suitable artifact rejection techniques. Having measured each Vpp EMG response (as facilitated by the stimulation and/or noise artifact rejection techniques), this Vpp information is then analyzed relative to the stimulation current in order to determine a relationship between the nerve and the given electrode on the surgical access instrument 46-50 transmitting the stimulation current. More specifically, the system 20 determines these relationships (between nerve and surgical accessory) by identifying the minimum stimulation current ($I_{Thresh}$) capable of producing a predetermined Vpp EMG response.

$I_{Thresh}$ may be determined for each of the four orthogonal electrodes 1402A-1402D (FIGS. 14A-14B) in an effort to determine the direction between the surgical access instrument 34, 36 and the nerve. This may be accomplished by employing a two-part threshold-hunting algorithm, including a bracketing process and a bi-section (or bisecting) process, which may proceed step-wise for each stimulation electrode to provide successive directional information to the user.

Arc Method

In one embodiment, successive directional information may take the form of an arc or wedge (or range) representing a zone that contains the nerve, according to an "arc" method described below. This successive directional information is based on stimulation current threshold "ranges," and may be displayed (FIGS. 15A-15C) or otherwise communicated to the surgeon any time the stimulation current thresholds are known to fall within a range of values.

In the bracketing process, an electrical stimulus is provided at each of the four orthogonal electrodes 1402A-1402D (FIGS. 14A-14B), beginning with a small current level (e.g. 0.2 mA) and ramping up. In the "arc" method, each of the four electrodes 1402A-1402D may be stimulated at the same current level, in sequence, before proceeding to the next higher current level (as opposed to another method that completes the bracketing for one electrode 1402 before advancing to another electrode 1402). The goal is to identify a bracket around the stimulation current for each of the four stimulation electrodes 1402A-1402D. If a stimulation current threshold has been bracketed for an electrode 1402, the bracketing act is complete for that electrode 1402, and stimulation proceeds for the remaining electrodes until the stimulation current threshold has been bracketed for each electrode. As the bracketing process proceeds, each new stimulation provides information about the "range" of the current threshold for that electrode 1402. This information may bracket the stimulation current threshold (e.g., between 1.6 and 3.2 mA), or it may only provide a lower bound for the current threshold (e.g., threshold is greater than 5.0 mA). In either event, the "arc" bracketing process proceeds for each of the stimulation electrodes 1402A-1402D to provide, in succession, more accurate information regarding the direction of the nerve relative to the surgical access instrument 46-50.

Figure 10:
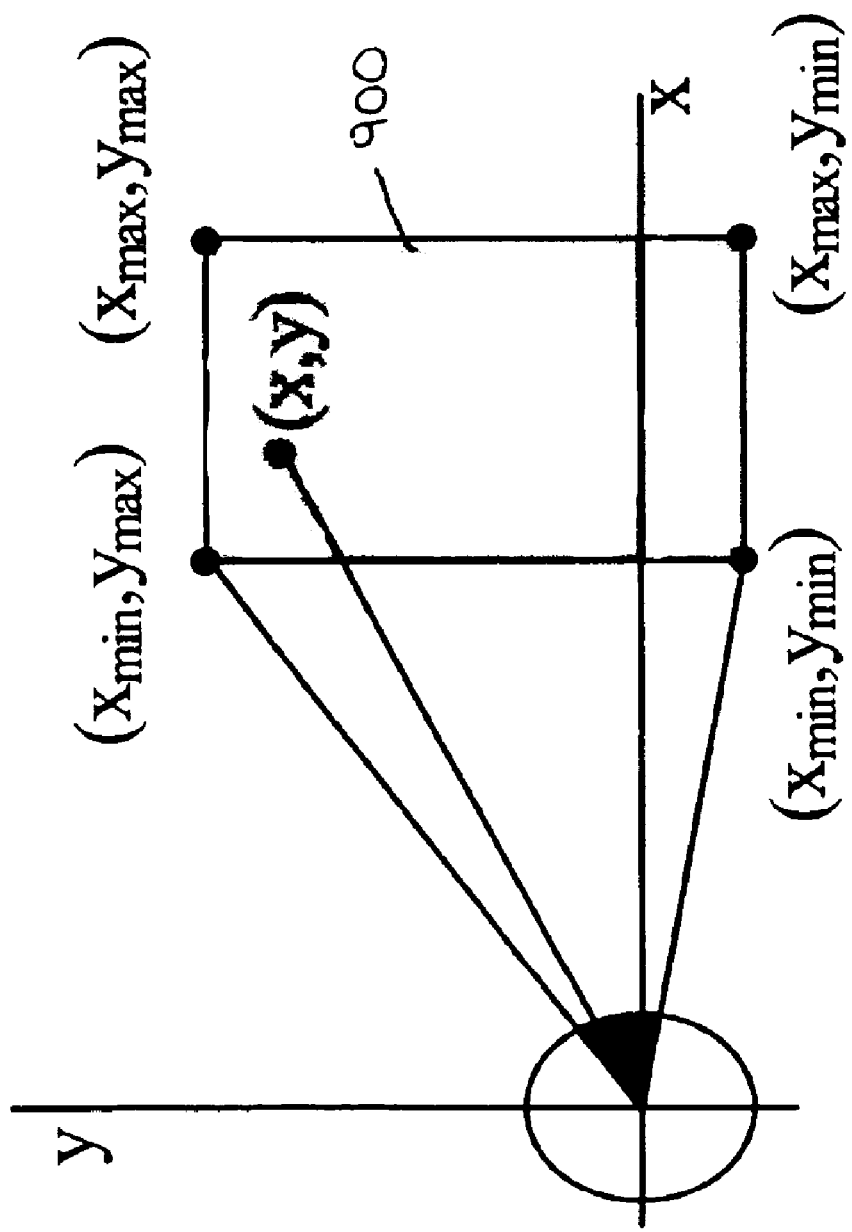
FIG. 10 illustrates a vector from an origin (center axis of an instrument with electrodes) to a nerve point (x, y) and an arc containing that vector found by the system of FIG. 2.

As shown in FIG. 10, an arc (wedge) containing the final direction vector is computed from the range information for the stimulation current thresholds corresponding to the four stimulation electrodes 1402A-1402D. This can be done as often as desired as the bracketing method proceeds. The arc (wedge) may then be used to display directional information to the operator, as in FIGS. 15A-15C.

Figure 15A:
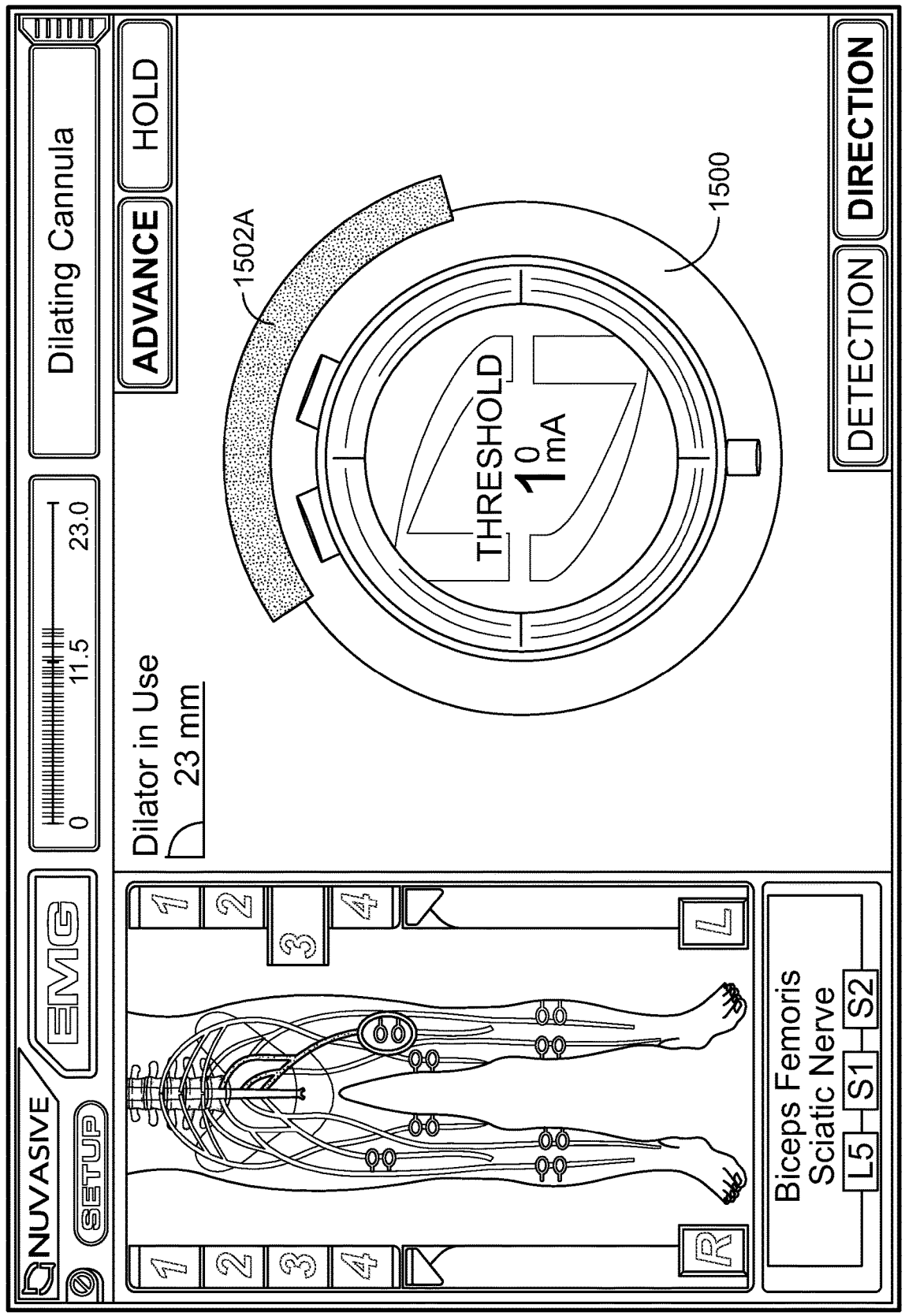
FIG. 15A-15C are displays of a surgical instrument in FIG. 2 and a nerve direction arc that may become progressively smaller until it becomes an arrow as stimulation threshold levels are bracketed, bisected and found for a plurality of electrodes in FIGS. 14A-14B.
Figure 15B:
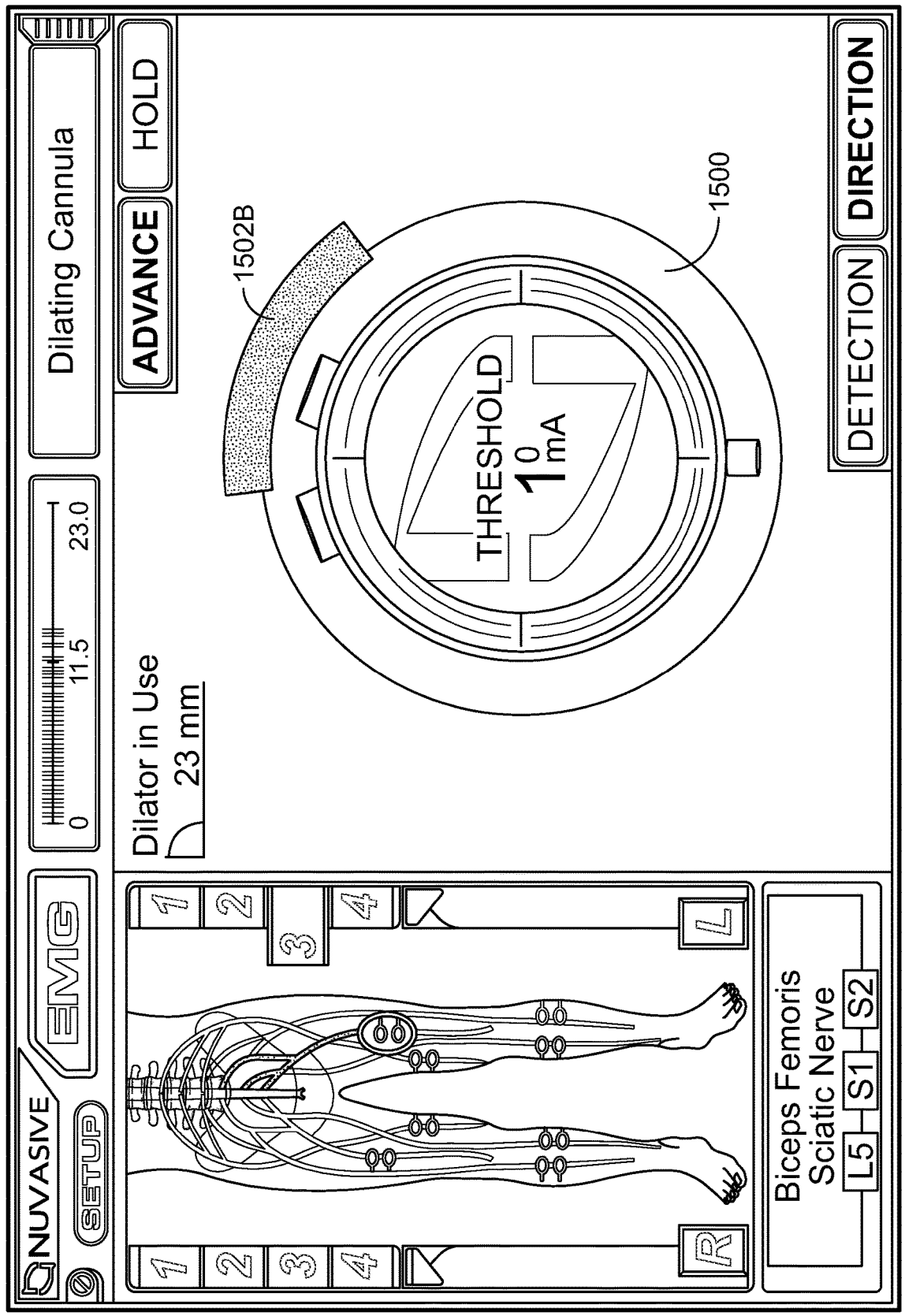
Figure 15C:
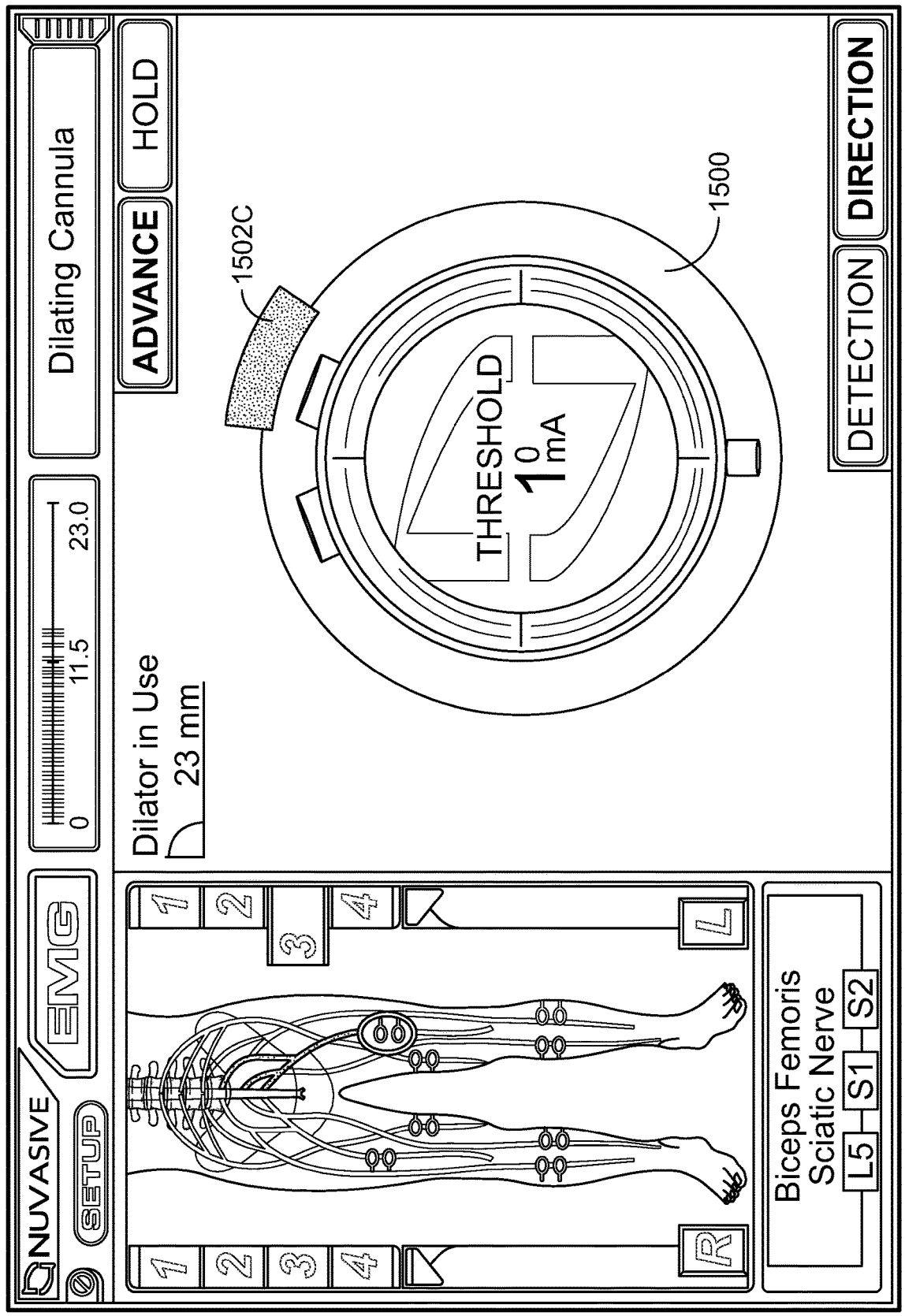

This successive approximation information may be communicated to the surgeon in a number of easy-to-interpret fashions, including but not limited to the use of visual indicia (such as alpha-numeric characters, light-emitting elements, and/or graphics, as in FIGS. 15A-15C and 20-21) and audio communications (such as a speaker element 18 in FIG. 3). By way of example only, this successive directional information may include providing an "arc" 1502 (hence the name "arc" method) or other graphical representation that indicates the general direction to the nerve, which may start off relatively wide, become successively more narrow (based on improved accuracy over time), and may conclude with a single arrow designating the relative direction to the nerve. FIGS. 15A-15C illustrate screenshots of a cross-section of an instrument 1500 and a wide direction arc 1502A, a narrower direction arc 1502B and an arrow 1502C as more stimulation current pulses are generated and EMG responses are analyzed during the bracketing and bisecting processes.

There are a number of possibilities for displaying the arc information. An arc or wedge might be displayed. Alternatively, an arrow might point to the midpoint of the arc. Another indicator might be used to illustrate the width of the arc (i.e. the uncertainty remaining in the result).

Upon completion of the bracketing process, a bisection process may determine more precisely the stimulation current thresholds. As with the bracketing process, current stimulations may be "rotated" among the stimulation electrodes so that the thresholds are refined substantially in parallel, according to the "arc" method. As with the bracketing method, the arc (wedge) 1502 containing the final direction vector may be computed and displayed (FIGS. 15A-15C) frequently during the process. Upon completion of the bisection method for all electrodes 1402A-1402D, the stimulation current thresholds are identified precisely. At that time, the final direction vector 1502C (FIG. 15C and FIGS. 20-21) may be displayed.

The above-identified two-part hunting-algorithm may be further explained with reference to FIGS. 7A-7E. According to the arc method, each electrode 1402 is stimulated at the same stimulation current level before passing to the next stimulation current level. In this fashion, successive directional information can be obtained as described above. Threshold current ($I_{Thresh}$) is the minimum stimulation current ($I_{Stim}$) (FIG. 6) that produces a Vpp (FIG. 5) greater than a known threshold voltage ($V_{Thresh}$). The value of $I_{Stim}$ may be adjusted by a bracketing method as follows. The first bracket may be 0.2 mA and 0.3 mA. If the Vpp corresponding to both of these stimulation currents is lower than Vthresh, then the bracket size may be doubled to 0.2 mA and 0.4 mA. This doubling of the bracket size continues until the upper end of the bracket results in a Vpp that is above $V_{Thresh}$.

The size of the brackets may then be reduced by a bisection method. A current stimulation value at the midpoint of the bracket is used, and if this results in a Vpp that is above Vthresh, then the lower half becomes the new bracket. Likewise, if the midpoint Vpp is below Vthresh, then the upper half becomes the new bracket. This bisection method is used until the bracket size has been reduced to $I_{Thresh}$ mA. $I_{Thresh}$ may be selected as a value falling within the bracket, but is preferably defined as the midpoint of the bracket.

The threshold-hunting algorithm of this embodiment may support three states: bracketing, bisection, and monitoring. A "stimulation current bracket" is a range of stimulation currents that bracket the stimulation current threshold $I_{Thresh}$. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method described herein to select stimulation currents and identify stimulation current brackets for each EMG channel in range.

The initial bracketing range may be provided in any number of suitable ranges. In one embodiment, the initial bracketing range is 0.2 to 0.3 mA. If the upper stimulation current does not evoke a response, the upper end of the range should be increased. For example, the range scale factor may be 2. The stimulation current should preferably not be increased by more than 10 mA in one iteration. The stimulation current should preferably never exceed a programmed maximum stimulation current (to prevent nerve damage, injury or other undesirable effects). For each stimulation, the algorithm will examine the response of each active channel to determine whether the stimulation current falls within that bracket. Once the stimulation current threshold of each channel has been bracketed, the algorithm transitions to the bisection state.

During the bisection state (FIGS. 7C and 7D), threshold hunting may select stimulation currents and narrow the bracket to a selected width (for example, 0.1 mA) for each EMG channel with an in-range threshold. After the minimum stimulation current has been bracketed (FIG. 7B), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The nerve proximity/direction detection algorithm is locked on the electrode position when the response threshold is bracketed by stimulation currents separated by the selected width (i.e., 0.1 mA). The process is repeated for each of the active channels until all thresholds are precisely known. At that time, the algorithm may enter the monitoring state.

During the monitoring state (FIG. 7E), threshold hunting may employ the method described below to select stimulation currents and identify whether stimulation current thresholds are changing. In the monitoring state, the stimulation current level may be decremented or incremented by 0.1 mA, depending on the response of a specific channel. If the threshold has not changed, then the lower end of the bracket should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm may transition back to the bracketing state in order to reestablish the bracket.

Figure 8:
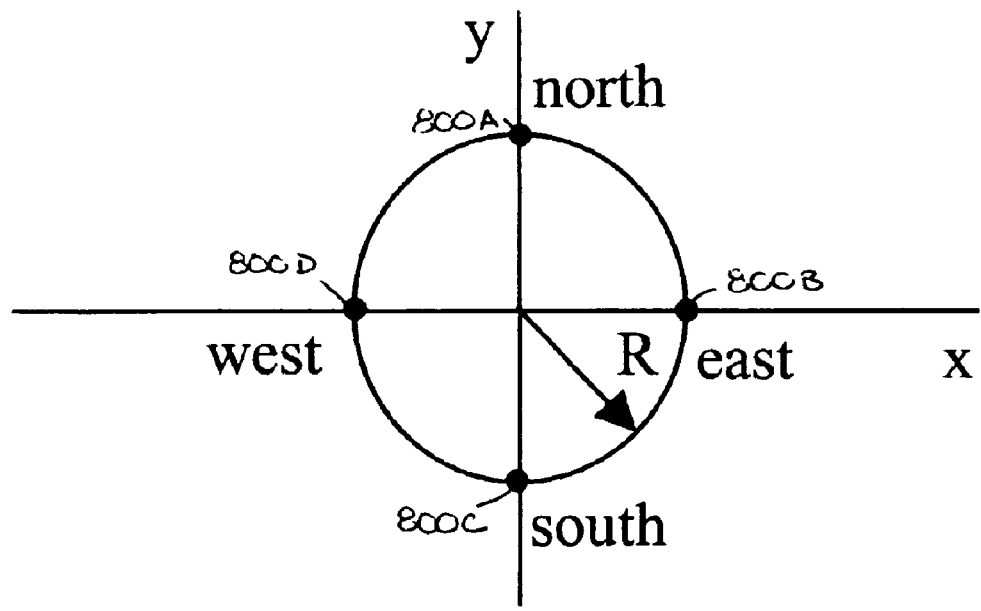
FIG. 8 illustrates four orthogonal electrodes near a distal end of a surgical instrument, such as a cannula, modeled as north, south, east and west points in a two-dimensional X-Y plane for the system of FIG. 2.

A method for computing the successive arc/wedge directional information from stimulation current threshold range information is described. The stimulation current threshold is presumed to be proportional to a distance to the nerve. The nerve may be modeled as a single point. Since stimulation current electrodes are in an orthogonal array, calculation of the X- and Y-dimension components of the direction vector may proceed independently. With reference to FIG. 8, the North and South electrodes 800A, 800C contribute to the Y-dimension component, while the East and West electrodes 800B-800D contribute to the X-dimension component. The direction vector <x, y> to a nerve may be defined as:

$$x = i_w^2 - i_e^2$$
$$y = i_s^2 - i_n^2 \quad (1)$$

where $i_e$, $i_w$, $i_n$, and $i_s$ represent the stimulation current thresholds for the east, west, north, and south electrodes 802B, 802D, 802A, 802C, respectively. (The equations may be normalized to an arbitrary scale for convenience.)

As the threshold hunting method begins, the stimulation current thresholds are known only within a range of values. Therefore, the X- and Y-dimension components are known only within a range. This method provides an extension to the previous definitions, as follows:

$$x_{min} = i_{w,min}^2 - i_{e,max}^2$$
$$x_{max} = i_{w,max}^2 - i_{e,min}^2$$
$$y_{min} = i_{s,min}^2 - i_{n,max}^2$$
$$y_{max} = i_{s,max}^2 - i_{n,min}^2 \quad (2)$$

Figure 9:
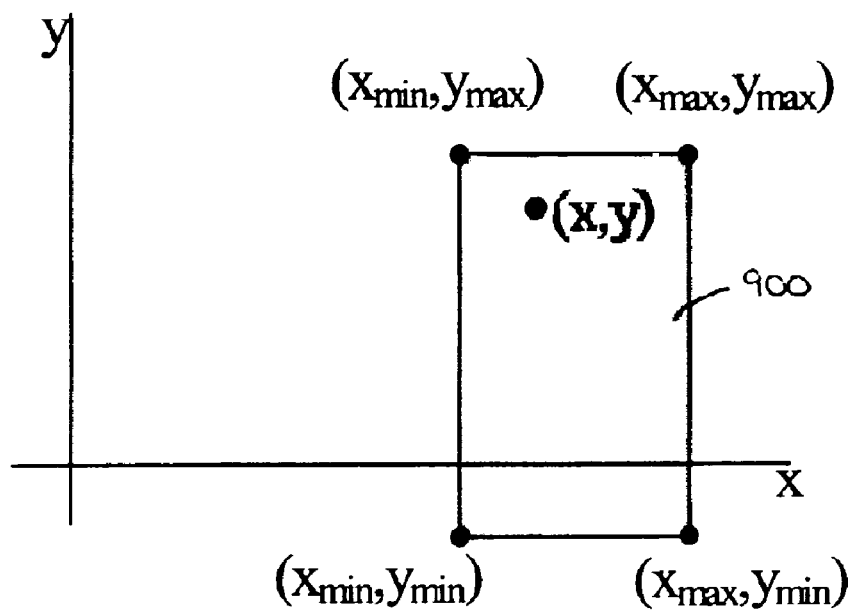
FIG. 9 illustrates a nerve point (x, y) bounded by maximum and minimum x- and y-values, which forms a rectangle.

Just as $i_{e,min}$ and $i_{e,max}$ bracket $i_e$, x and y are bracketed by $[x_{min}, x_{max}]$ and $[y_{min}, y_{max}]$. Stated another way, the point (x,y) lies within a rectangle 900 described by these boundaries, as shown in FIG. 9. As shown in FIG. 10, just as the point (x,y) represents a vector from the origin to a nerve modeled as a point, the bounding rectangle 900 represents an arc (wedge) containing that vector.

The arc method may have several advantages. First, the arc is capable of narrowing in a relatively quick fashion as more stimulations and responses are analyzed. This method provides general directional information much faster than if the current threshold for each electrode 1402 was determined before moving on the next electrode 1402. With general directional information, it may be possible to terminate the stimulation before having the ultimate precision of the stimulation current vectors. This will result in a faster response, in many instances. The arc method may provide a real-time view of the data-analysis. This helps illustrate the value of additional stimulations to a user. This educates and empowers the user. The user can observe the progress of this method, which aids in the understanding of the time the system 20 takes to converge on the final direction vector. More frequent display updates help time "go faster" for the user. This method avoids a long pause that might seem even longer. Disclosure of the intermediate acts (narrowing arcs) in the process of finding the direction vector invites mutual trust between the user and the access system 30. An arc may provide a more intuitive visualization for neural tissue than a direction vector.

The arc method may also be useful in tracking direction as the instrument and stimulation electrodes move relative to the nerve. For example, if the uncertainty in the stimulation current threshold increases, this can be reflected in an increasing arc size.

The sequential dilation access system 34 (FIG. 2) of the system 20 is capable of accomplishing safe and reproducible access to a surgical target site. It does so by detecting the existence of and direction to neural structures before, during, and after the establishment of an operative corridor through (or near) any of a variety of tissues having such neural structures. If neural structures are contacted or impinged, this may result in neural impairment for the patient.

In one embodiment, the surgical system 20 accomplishes this through the use of the surgical hand-piece 52, which may be electrically coupled to the K-wire 46 via a first cable connector 51a, 51b and to either the dilating cannula 48 or the working cannula 50 via a second cable connector 53a, 53b. For the K-wire 46 and working cannula 50, cables are directly connected between these accessories and the respective cable connectors 51a, 53a for establishing electrical connection to the stimulation electrode(s). In one embodiment, a pincher or clamp-type device 57 is provided to selectively establish electrical communication between the surgical hand-piece 52 and the stimulation electrode(s) on the distal end of the cannula 48. This is accomplished by providing electrical contacts on the inner surface of the opposing arms forming the clamp-type device 57, wherein the contacts are dimensioned to be engaged with electrical contacts (preferably in a male-female engagement scenario) provided on the dilating cannula 48 and working cannula 50. The surgical hand-piece 52 includes one or more buttons such that a user may selectively direct a stimulation current signal from the control unit 22 to the electrode(s) on the distal ends of the surgical access components 46-50. In an important aspect, each surgical access component 46-50 is insulated along its entire length, with the exception of the electrode(s) at their distal end. In the case of the dilating cannula 48 and working cannula 50, the electrical contacts at their proximal ends for engagement with the clamp 57 are not insulated. The EMG responses corresponding to such stimulation may be monitored and assessed in order to provide nerve proximity and/or nerve direction information to the user.

Figure 11:
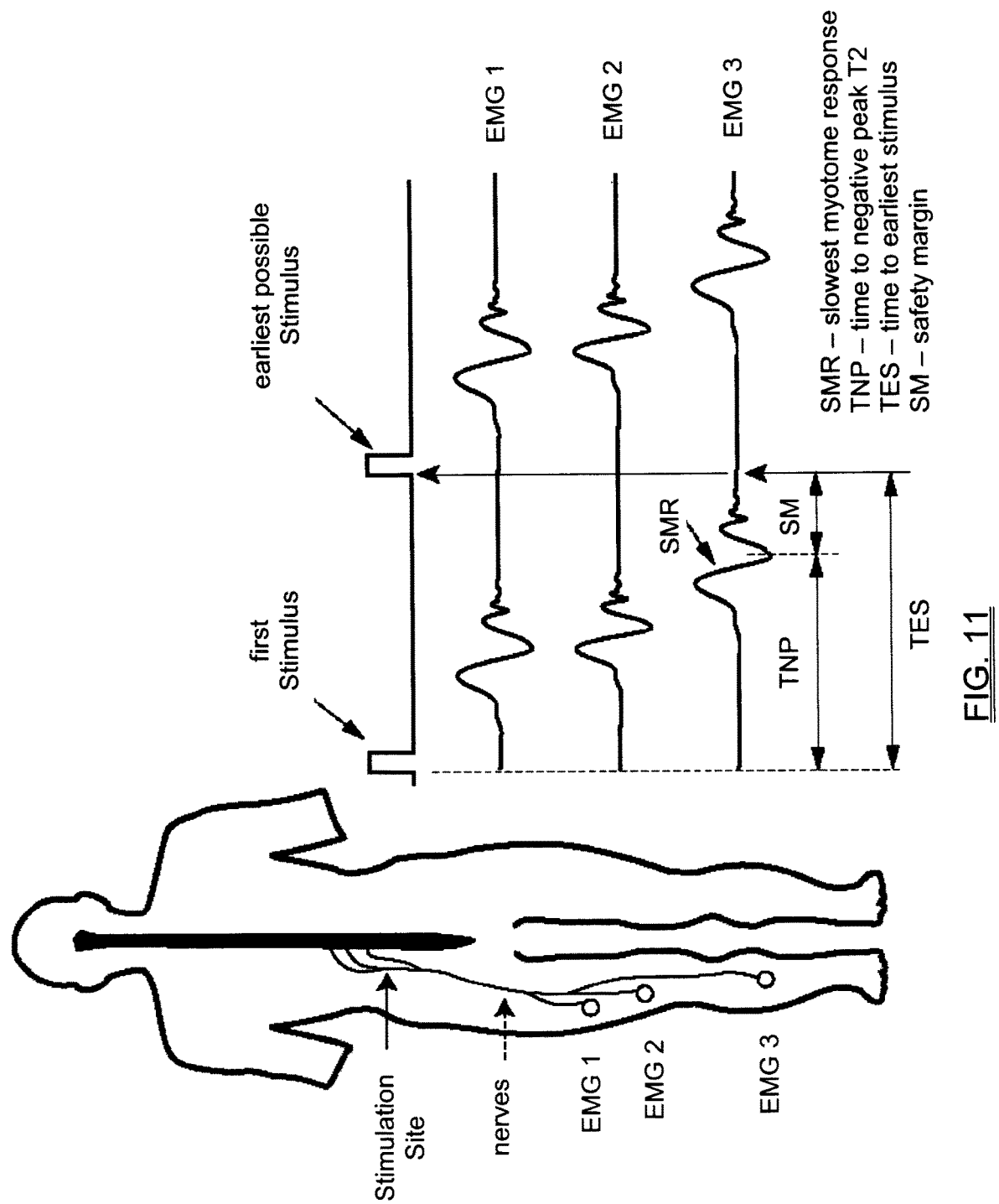
FIG. 11 illustrates a stimulation site and multiple EMG response sensing sites for the system of FIG. 2.
Figure 12:
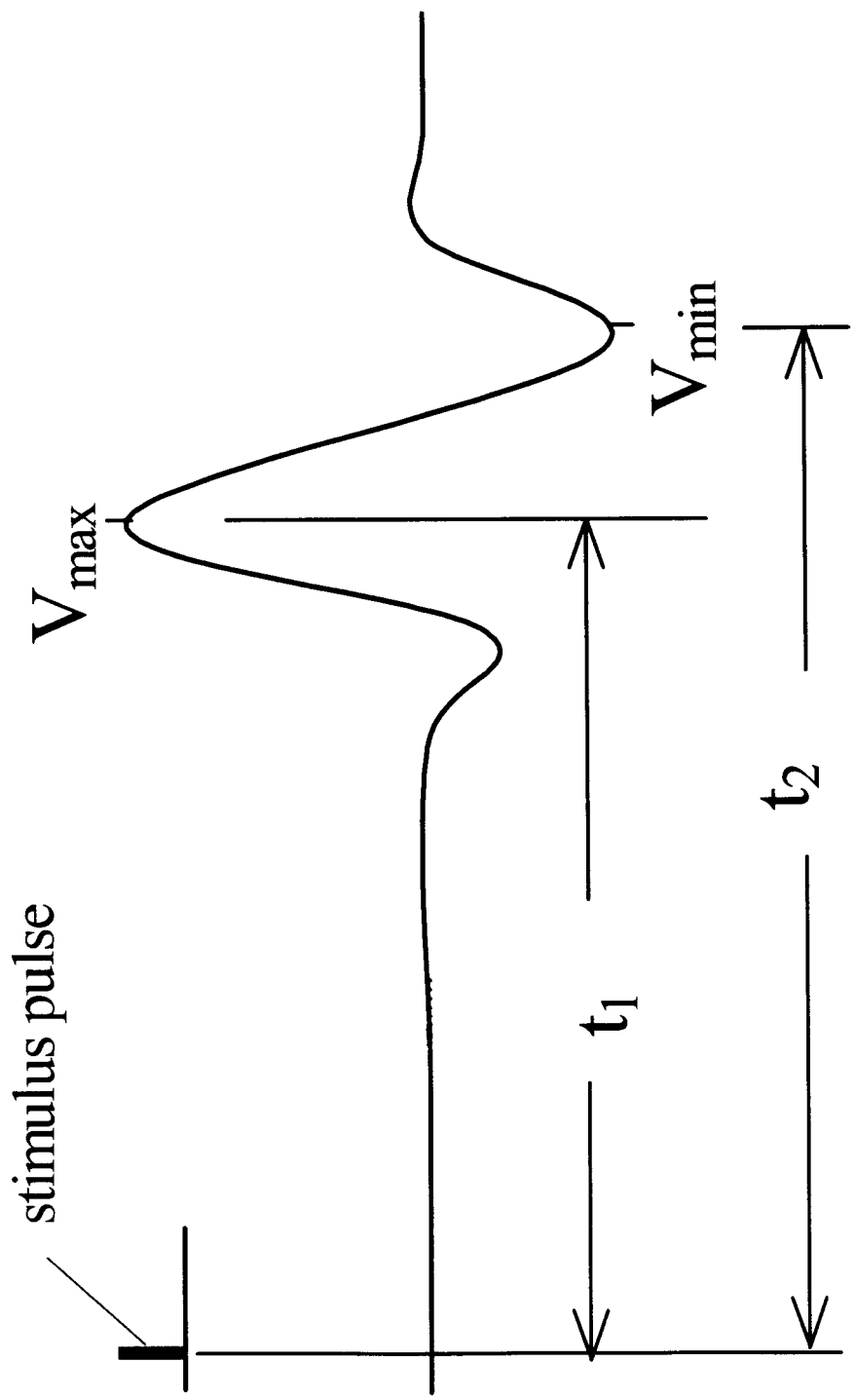
FIG. 12 is a graph illustrating a plot of a neuromuscular response (EMG) over time in response to a stimulus current pulse, where the plot shows voltage extrema at times T1 and T2.
Figure 20:
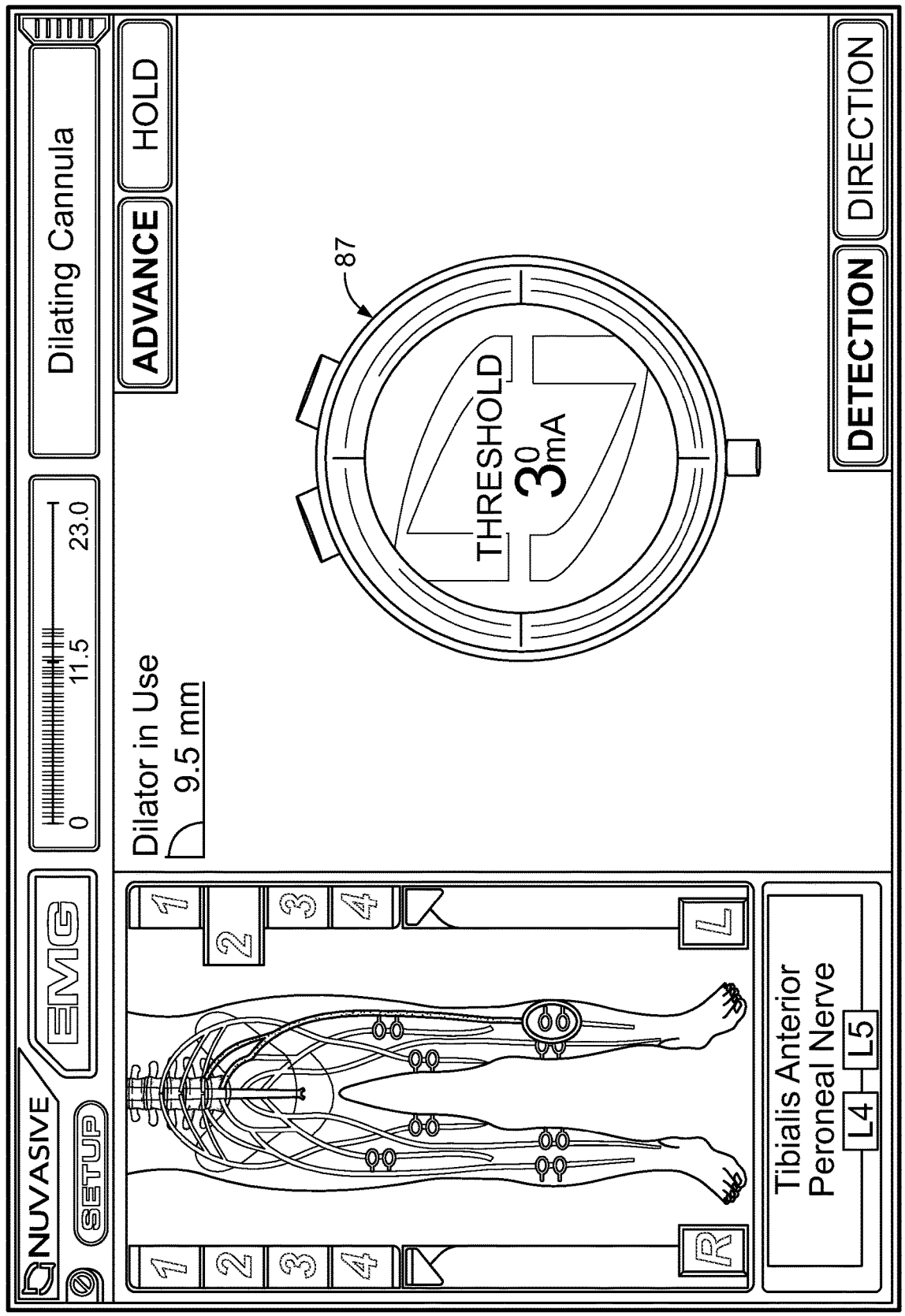
FIGS. 20-21 are exemplary screen displays illustrating one embodiment of the nerve direction feature of the surgical access system of FIG. 2.
Figure 21:
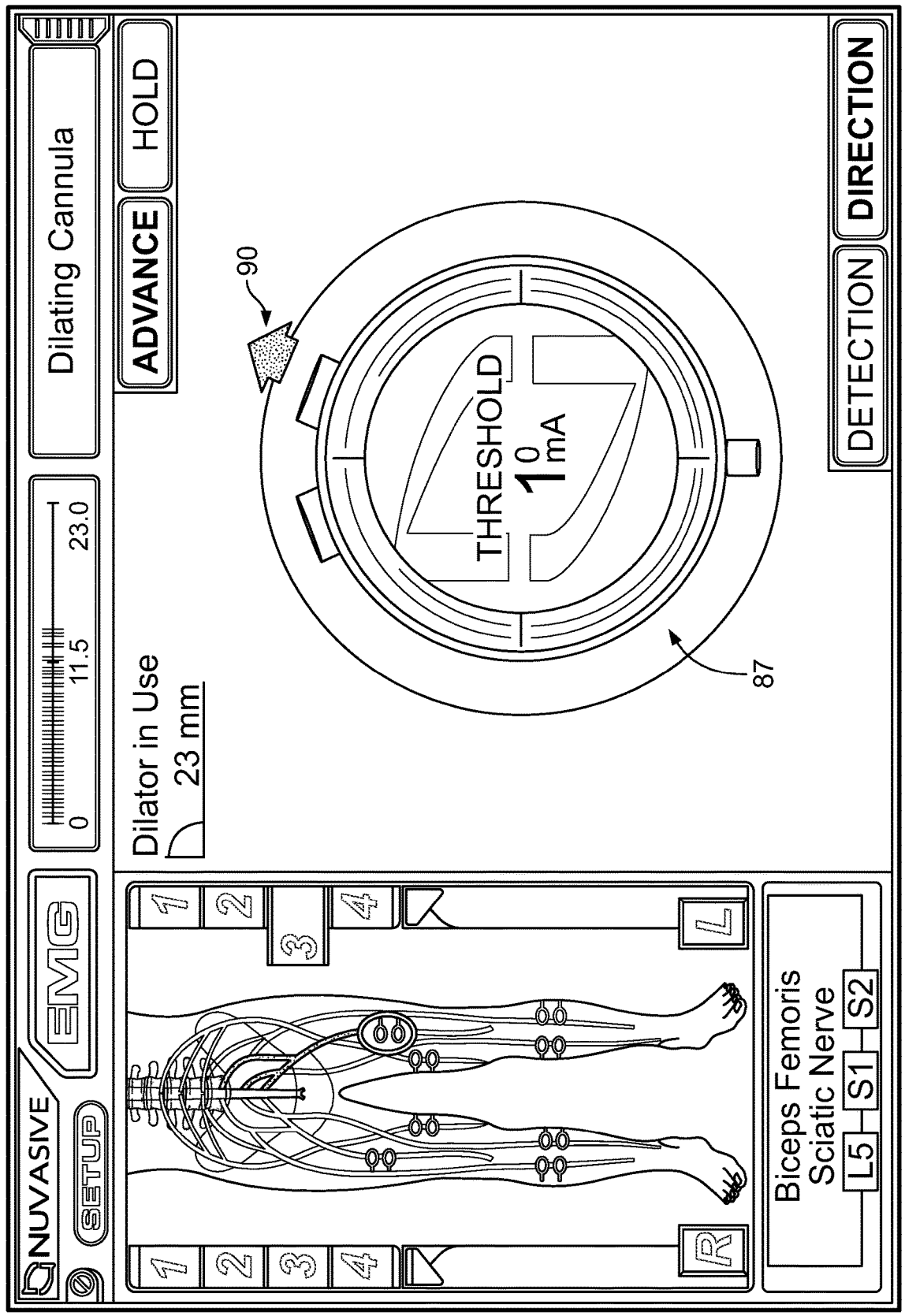

When employed in spinal procedures, for example, such EMG monitoring would preferably be accomplished by connecting the EMG harness 26 to the myotomes in the patient's legs corresponding to the exiting nerve roots associated with the particular spinal operation level (see FIGS. 11 and 20-21). In a preferred embodiment, this is accomplished via 8 pairs of EMG electrodes 27 (FIG. 2) placed on the skin over the major muscle groups on the legs (four per side), an anode electrode 29 providing a return path for the stimulation current, and a common electrode 31 providing a ground reference to pre-amplifiers in the patient module 24. Although not shown, it will be appreciated that any of a variety of electrodes can be employed, including but not limited to needle electrodes. The EMG responses measured via the EMG harness 26 provide a quantitative measure of the nerve depolarization caused by the electrical stimulus. By way of example, the placement of EMG electrodes 27 may be undertaken according to the manner shown in Table 1 below for spinal surgery:

TABLE 1

| Color | Channel ID | Myotome | Spinal Level |
| --- | --- | --- | --- |
| Blue | Right 1 | Right Vastus Medialis | L2, L3, L4 |
| Violet | Right 2 | Right Tibialis Anterior | L4, L5 |
| Grey | Right 3 | Right Biceps Femoris | L5, S1, S2 |
| White | Right 4 | Right Gastroc. Medial | S1, S2 |
| Red | Left 1 | Left Vastus Medialis | L2, L3, L4 |
| Orange | Left 2 | Left Tibialis Anterior | L4, L5 |
| Yellow | Left 3 | Left Biceps Femoris | L5, S1, S2 |
| Green | Left 4 | Left Gastroc. Medial | S1, S2 |

Figure 16:
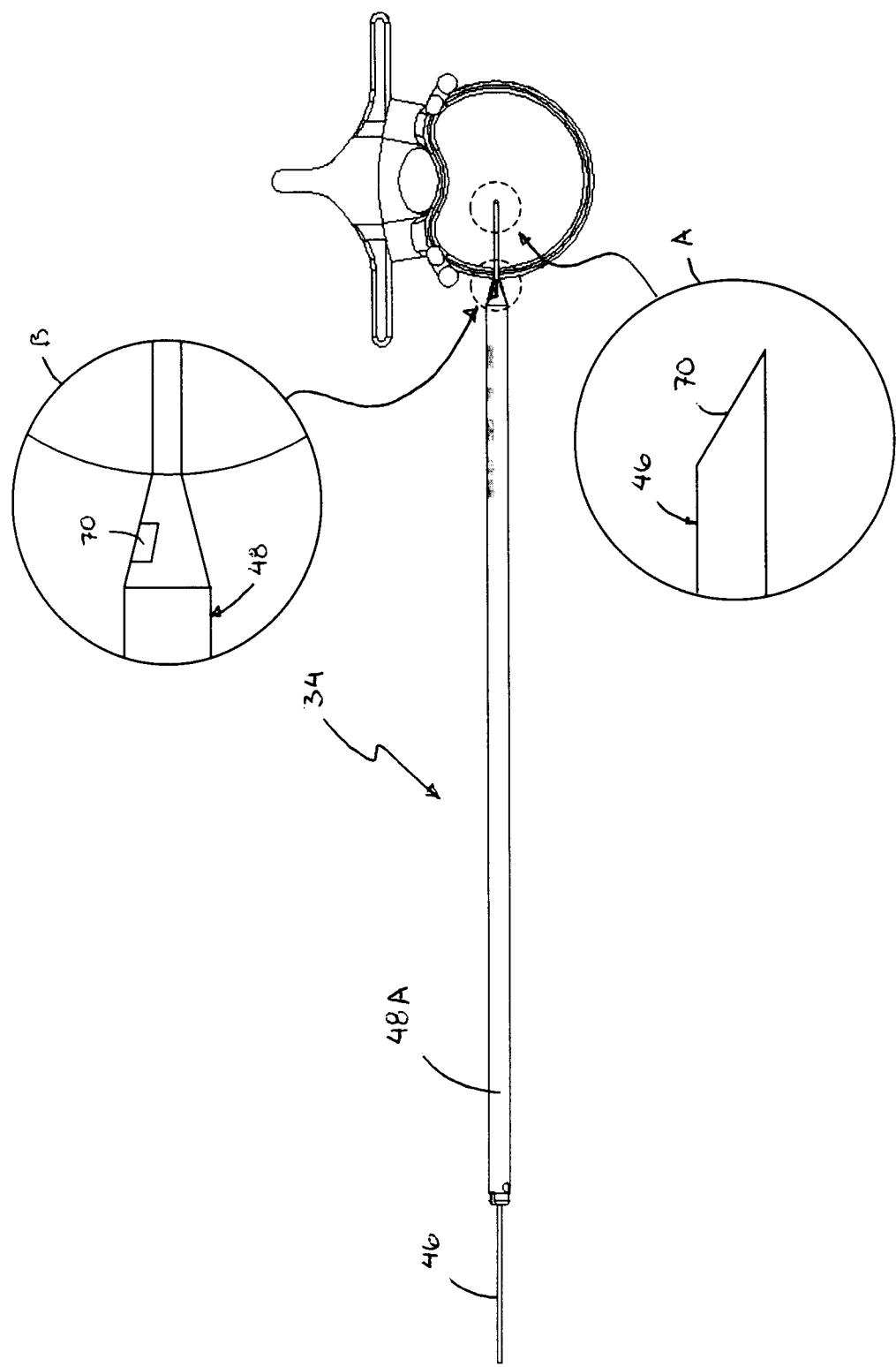
FIGS. 16-19 illustrate a sequential dilation access system of FIG. 2 in use creating an operative corridor to an intervertebral disk.

FIGS. 16-19 illustrate the sequential dilation access system 34 in FIG. 2 in use creating an operative corridor to an intervertebral disk. As shown in FIG. 16, an initial dilating cannula 48A is advanced towards the target site with the K-wire 46 disposed within an inner lumen within the dilating cannula 48. This may be facilitated by first aligning the K-wire 46 and initial dilating cannula 48A using any number of commercially available surgical guide frames. In one embodiment, as best shown in the expanded insets A and B, the K-wire 46 and initial dilating cannula 48A are each equipped with a single stimulation electrode 70 to detect the presence and/or location of nerves in between the skin of the patient and the surgical target site. More specifically, each electrode 70 may be positioned at an angle relative to the longitudinal axis of the K-wire 46 and dilator 48 (and working cannula 50). In one embodiment, this angle may range from 5 to 85 degrees from the longitudinal axis of these surgical access components 46-50. By providing each stimulation electrode 70 in this fashion, the stimulation current will be directed angularly from the distal tip of the respective accessory 46, 48. This electrode configuration is advantageous in determining proximity, as well as direction, according to the present application in that a user may simply rotate the K-wire 46 and/or dilating cannula 48 while stimulating the electrode 70. This may be done continuously or step-wise, and preferably while in a fixed axial position. In either case, the user will be able to determine the location of nerves by viewing the proximity information on the display screen 40 and observing changes as the electrode 70 is rotated. This may be facilitated by placing a reference mark 72 on the K-wire 46 and/or dilator 48 (or a control element coupled thereto), indicating the orientation of the electrode 70 to the user.

In another embodiment, the K-wire 46 and dilating cannula 48 in FIG. 2 may each have multiple electrodes, as described above and shown in FIGS. 14A-14B.

Figure 17:
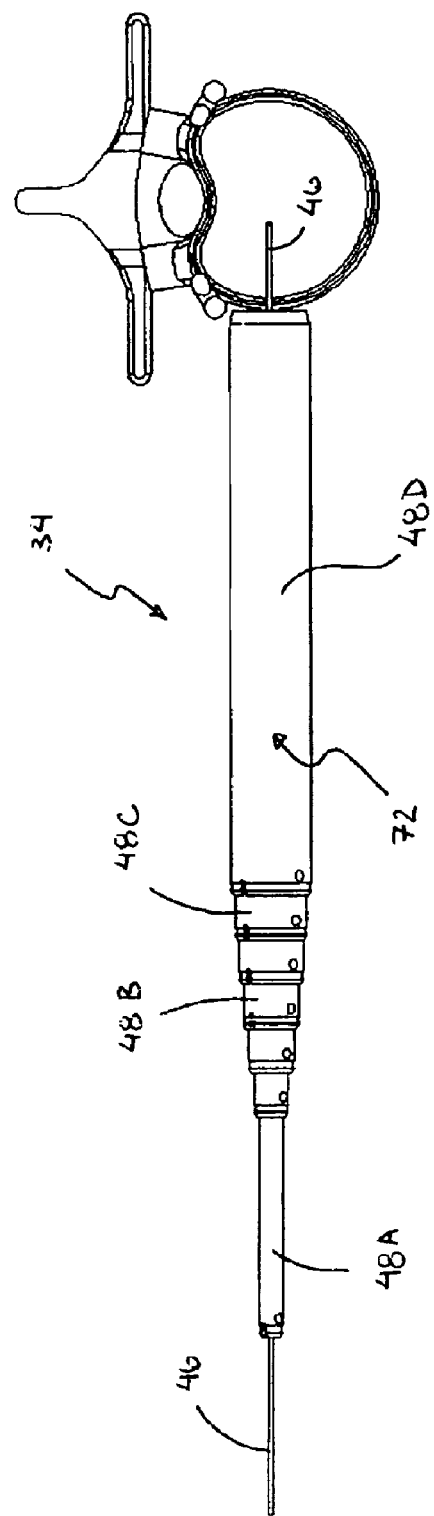
Figure 18:
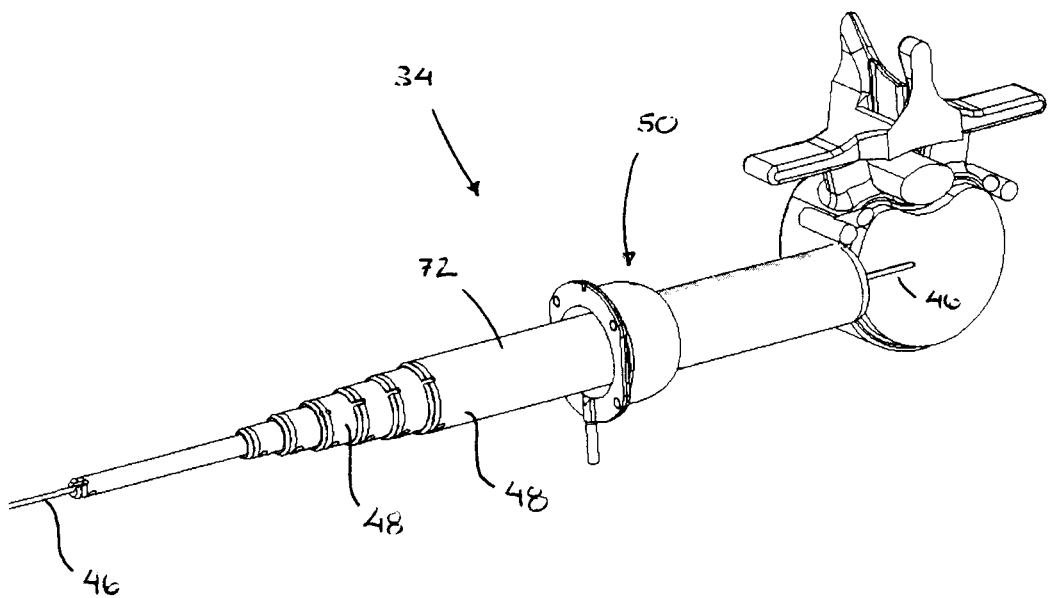
Figure 19:
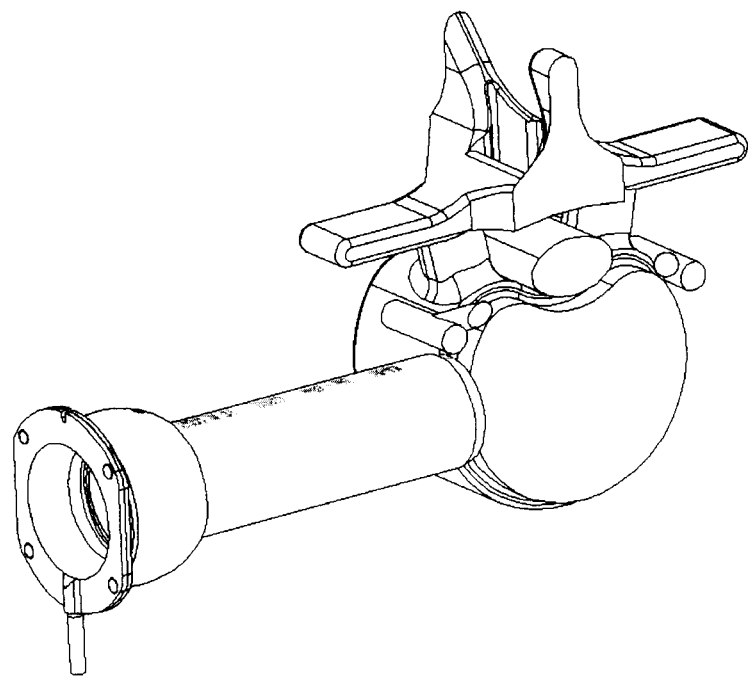

In the embodiment shown, the trajectory of the K-wire 46 and initial dilator 48A is such that they progress towards an intervertebral target site in a postero-lateral, trans-psoas fashion so as to avoid the bony posterior elements of the spinal column. Once the K-wire 46 is docked against the annulus of the particular intervertebral disk, cannulae of increasing diameter 48B-48D may then be guided over the previously installed cannula 48A (sequential dilation) until a desired lumen diameter is installed, as shown in FIG. 17. By way of example only, the dilating cannulae 48A-48D may range in diameter from 6 mm to 30 mm, with length generally decreasing with increasing diameter size. Depth indicia 72 may be optionally provided along the length of each dilating cannula 48 to aid the user in gauging the depth between the skin of the patient and the surgical target site. As shown in FIG. 18, the working cannula 50 may be slideably advanced over the last dilating cannula 48D after a desired level of tissue dilation has been achieved. As shown in FIG. 19, the last dilating cannula 48D and then all the dilating cannulae 48 may then be removed from inside the inner lumen of the working cannula 50 to establish the operative corridor therethrough.

Figure 13:
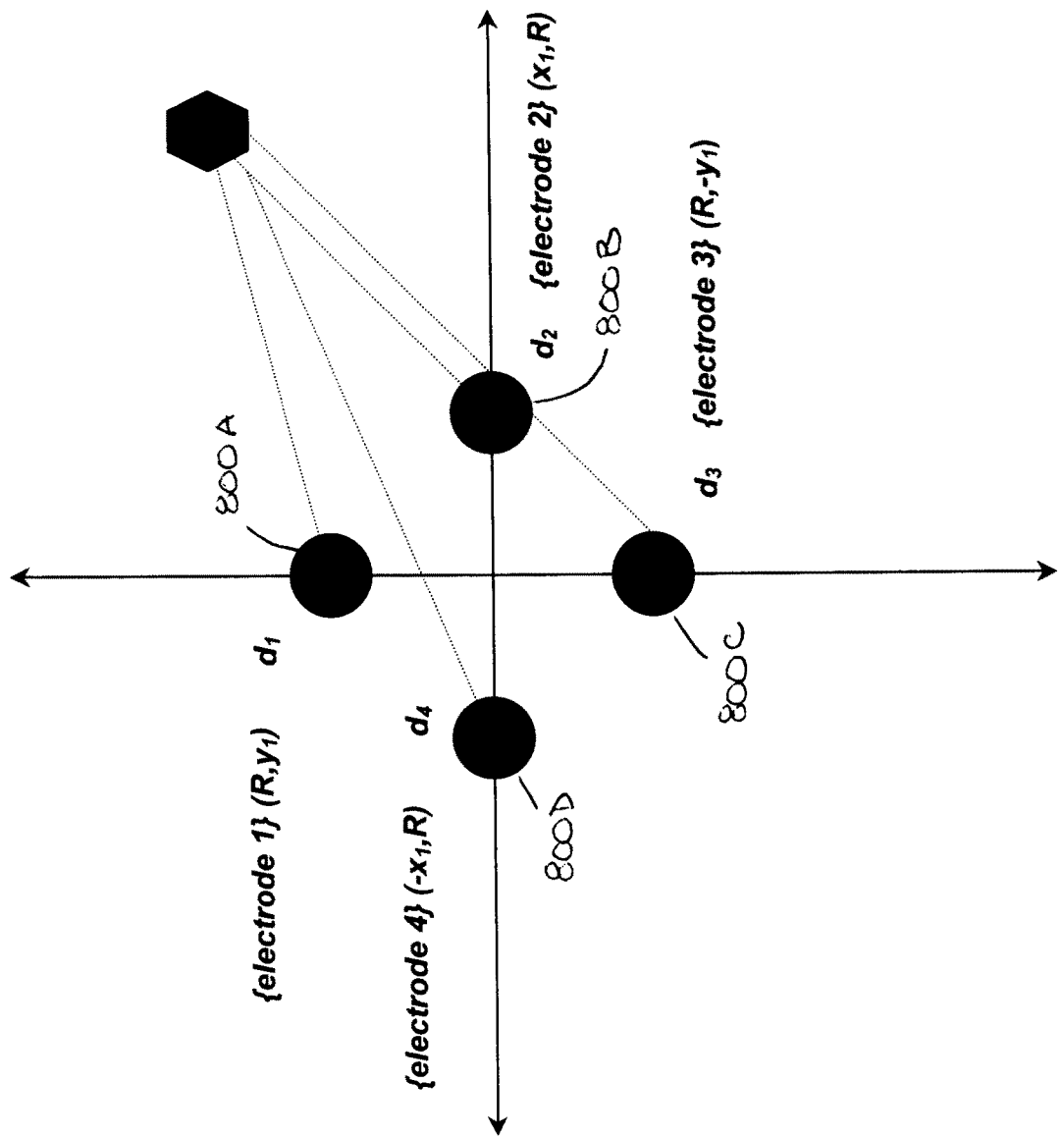
FIG. 13 is a graph illustrating a method of determining the direction of a nerve (denoted as a "hexagon") relative to an instrument having four (4) orthogonally disposed stimulation electrodes (denoted by the "circles") for the system of FIG. 2.
Figure 14A:
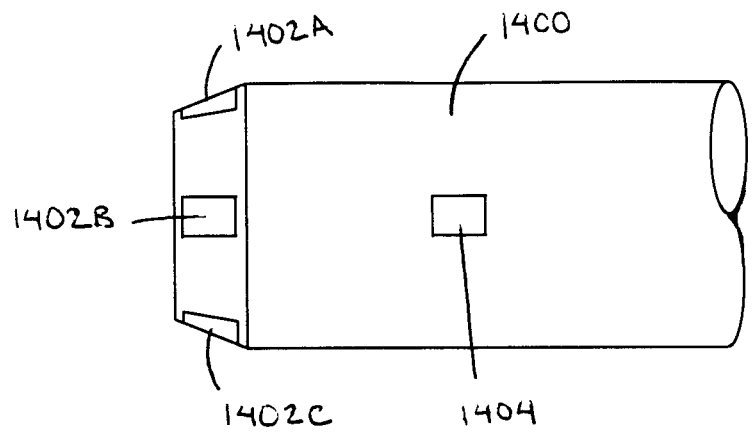
FIG. 14A is a side view and FIG. 14B is a front view of a distal end of a surgical instrument, such as a cannula in FIG. 2, with four orthogonal electrodes and a fifth electrode.
Figure 14B:
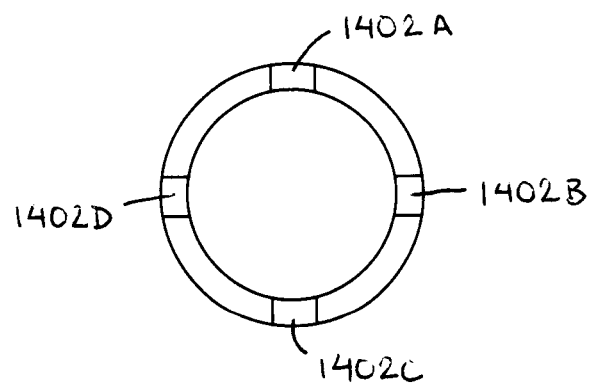

Once a nerve is detected using the K-wire 46, dilating cannula 48, or the working cannula 50, the surgeon may select the DIRECTION function to determine the angular direction to the nerve relative to a reference mark on the access components 46-50, as shown in FIG. 21. In one embodiment, a directional arrow 90 is provided, by way of example only, disposed around the cannula graphic 87 for the purpose of graphically indicating to the user which direction the nerve is relative to the access components 46-50. This information helps the surgeon avoid the nerve as he or she advances the K-wire 46 and cannulae 48, 50. In one embodiment, this directional capability is accomplished by equipping the K-wire 46, dilators 48 and working cannula 50 with four (4) stimulation electrodes disposed orthogonally on their distal tip (FIGS. 14A-14B). These electrodes are preferably scanned in a monopolar configuration (that is, using each of the 4 electrodes as the stimulation source). The threshold current ($I_{thresh}$) is found for each of the electrodes by measuring the muscle evoked potential response Vpp and comparing it to a known threshold Vthresh. From this information, the direction from a stimulation electrode (or device 46-50) to a nerve may be determined according to the algorithm and technique described herein and with reference to FIGS. 8-10, 13, 14A-14B and 15A-15C. In FIGS. 8 and 13, the four (4) electrodes 800A-800D are placed on the x and y axes of a two dimensional coordinate system at a radius R from the origin. A vector is drawn from the origin along the axis corresponding to each electrode. Each vector has a length equal to $I_{Thresh}$ for that electrode. Thus, with four electrodes 800A-800D, four vectors are drawn from the origin along the four axi corresponding to the four electrodes. The vector from the origin to a direction pointing toward the nerve is then computed. Using the geometry shown, the (x,y) coordinates of the nerve, taken as a single point, can be determined as a function of the distance from the nerve to each of four electrodes 800A-800D. This can be expressly mathematically as follows:

Where the "circles" in FIG. 13 denote the position of the electrode respective to the origin or center of the cannula, the "hexagon" denotes the position of a nerve, and $d_1$, $d_2$, $d_3$, and $d_4$ denote the distance between the nerve point and stimulation electrodes 1-4 (north, east, south and west) respectively, it can be shown that:

$$y = \frac{d_1^2 - d_3^2}{-4R} \text{ and } x = \frac{d_2^2 - d_4^2}{-4R}$$

Where R is the cannula radius, standardized to 1, since angles and not absolute values are measured.

After conversion from Cartesian coordinates (x,y) to polar coordinates (r,θ), then θ is the angular direction to the nerve. This angular direction may then be displayed to the user, by way of example only, as the arrow 90 shown in FIG. 21 pointing towards the nerve. In this fashion, the surgeon can actively avoid the nerve, thereby increasing patient safety while accessing the surgical target site. The surgeon may select any one of the 4 channels available to perform the Direction Function, although the channel with the lowest stimulation current threshold (that indicates a nerve closest to the instrument) should probably be used. The surgeon should preferably not move or rotate the instrument while using the Direction Function, but rather should return to the Detection Function to continue advancing the instrument.

After establishing an operative corridor to a surgical target site via the surgical access system 34, any number of suitable instruments and/or implants may be introduced into the surgical target site depending upon the particular type of surgery and surgical need. By way of example only, in spinal applications, any number of implants and/or instruments may be introduced through the working cannula 50, including but not limited to spinal fusion constructs (such as allograft implants, ceramic implants, cages, mesh, etc.), fixation devices (such as pedicle and/or facet screws and related tension bands or rod systems), and any number of motion-preserving devices (including but not limited to total disc replacement systems).

Segregating the Geometric and Electrical Direction Algorithm Models

There are other relationships resulting from the symmetry of the four electrodes described above:

$$d_w^2 + d_e^2 = d_s^2 + d_n^2 \quad (1)$$

and $$d_0^2 + R^2 = \frac{1}{4}(d_w^2 + d_e^2 + d_s^2 + d_n^2) \quad (2)$$

where do is the distance between the nerve activation site and the midpoint between the electrodes (i.e., the origin (0, 0) or "virtual center"). These results are based purely on geometry and apply independent of an electrical model.

As described above under the "arc" method, the geometric model can be extended to define a region of uncertainty based on the uncertainty in the distance to the nerve:

$$x_{min} = \frac{1}{4R}(d_{w,min}^2 - d_{e,max}^2) \quad (3)$$

$$x_{max} = \frac{1}{4R}(d_{w,max}^2 - d_{e,min}^2)$$

$$y_{min} = \frac{1}{4R}(d_{s,min}^2 - d_{n,max}^2)$$

$$y_{max} = \frac{1}{4R}(d_{s,max}^2 - d_{n,min}^2)$$

In FIGS. 8 and 13, the two-dimensional x-y model assumes that the nerve activation site lies in the same plane as the stimulation electrodes or the entire z-axis space may be considered to be projected onto the x-y plane. It has been found that the z-dimension has no effect on direction "in the plane." The distance equations presented in the previous sections also apply when the nerve activation site is out of the plane of the stimulation electrodes.

Generalized 1-D Model

Figure 22:
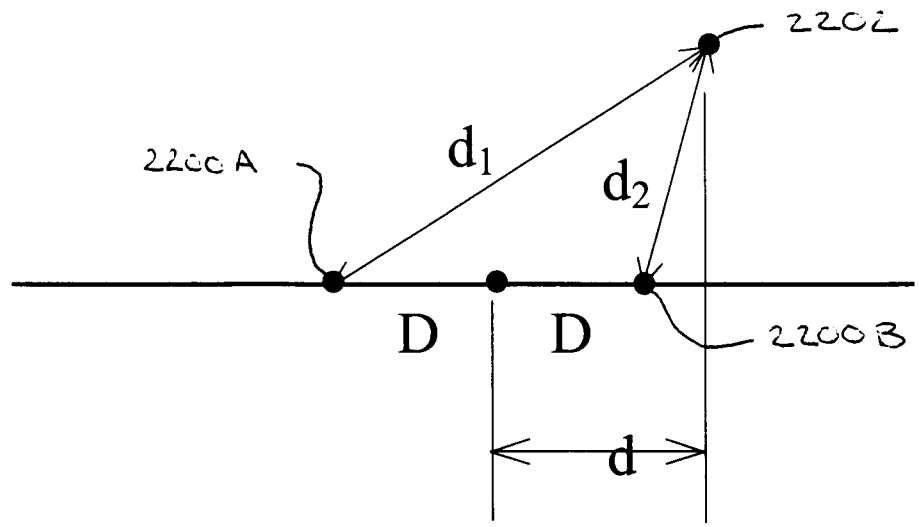
FIG. 22 illustrates a generalized one-dimensional, two-electrode, direction-finding model.

FIG. 22 illustrates two electrodes 2200A, 2200B. Given any two electrodes 2200A, 2200B, the absolute position of the nerve activation site 2202 in one dimension can be computed from the distances from those two electrodes:

$$d = \frac{1}{4D}(d_1^2 - d_2^2) \quad (4)$$

The 1-D model can be extended to two or three dimensions by the addition of electrodes.

3-D Geometric Model

Figure 23:
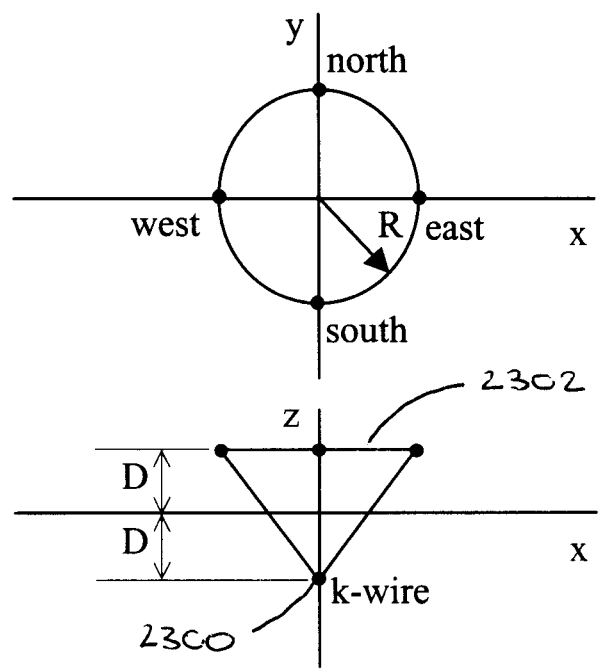
FIG. 23 illustrates an electrode positioned along the x=y=0 z-axis, which is in a different x-y plane than a plurality of other electrodes.

Using the four co-planar electrodes (FIGS. 8 and 13), it is not particularly easy to identify direction to the nerve along the z-axis. This may be easily rectified by the addition of one or more stimulation electrodes 2300 (FIG. 23) out of the original x-y electrode plane. For example, FIG. 23 shows a k-wire electrode 2300, positioned along the x=y=0 z-axis. D is half the distance between the K-wire electrode 2300 and the plane 2302 of the other four electrodes.

3-D direction to the nerve is possible by comparing the distance to the nerve activation site from the k-wire electrode 2300 to that of the other electrodes.

$$z = \frac{1}{4D}(d_o^2 - d_k^2) \quad (5)$$

where $d_o$ (as noted above) is the distance between the nerve activation site and the midpoint between the electrodes (i.e., the origin (0, 0) or "virtual center"), and $d_k$ is the distance between the nerve activation site and the k-wire electrode 2300. 3-D direction is possible by converting from Cartesian (x, y, z) to spherical (ρ, θ, φ) coordinates. The arc method described above may also be extended to three dimensions. Other 3-D geometric models may be constructed. One possibility is to retain the four planar electrodes 1402A-1402D and add a fifth electrode 1404 along the side of the cannula 1400, as shown in FIG. 14A.

Figure 25:
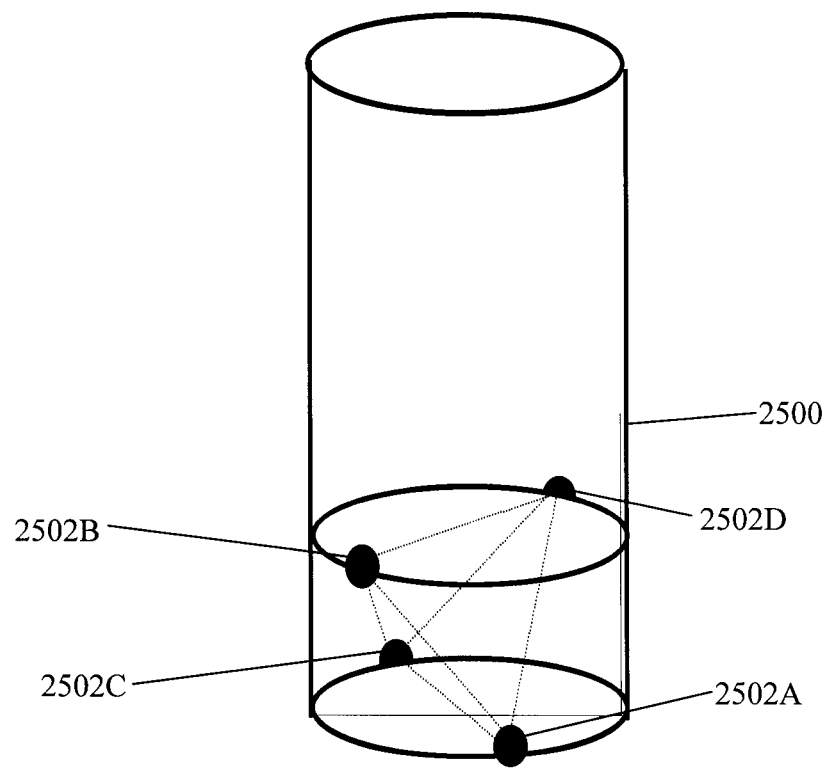
FIG. 25 illustrates a device with four electrodes in a tetrahedron configuration.

Another possibility is to replace the four planar electrodes 2502A-2502D with two pairs (e.g., vertices of a tetrahedron), as shown in FIG. 25. FIG. 25 illustrates a device 2500 with four electrodes 2502A-2502D in a tetrahedron configuration, which may be used with the system 20. Four electrodes may be a minimum for spanning a 3-D space, and may be the most efficient in terms of number of stimulations required to find the stimulation current thresholds.

Electric Model

The direction algorithm described above assumes direct proportionality between distance and the stimulation current threshold, as in equation (2).

$$i_{th} = Kd \quad (6)$$

where $i_{th}$ is the threshold current, K is a proportionality constant denoting a relationship between current and distance, and d is the distance between an electrode and a nerve.

An alternative model expects the stimulation current threshold to increase with the square of distance:

$$i_{th} = i_o Kd^2 \quad (7)$$

Using the distance-squared model, the Cartesian coordinates for the nerve activation site can be derived from equations (5), (7) and the following:

$$x = \frac{1}{4R}(d_w^2 - d_e^2) \quad (8)$$

$$y = \frac{1}{4R}(d_s^2 - d_n^2)$$

$$x = \frac{1}{4RK}(i_w - i_e)$$

$$y = \frac{1}{4RK}(i_s - i_n)$$

$$z = \frac{1}{4DK}(i_c - i_k)$$

where $i_x$ is the stimulation current threshold of the corresponding stimulation electrode (west, east, south or north), $i_k$ is the stimulation current threshold of the k-wire electrode 2602A (FIG. 26), and $i_c$ is calculated from:

$$i_c + KR^2 = \frac{1}{4}(i_w + i_e + i_s + i_n) \quad (9)$$

Figure 26:
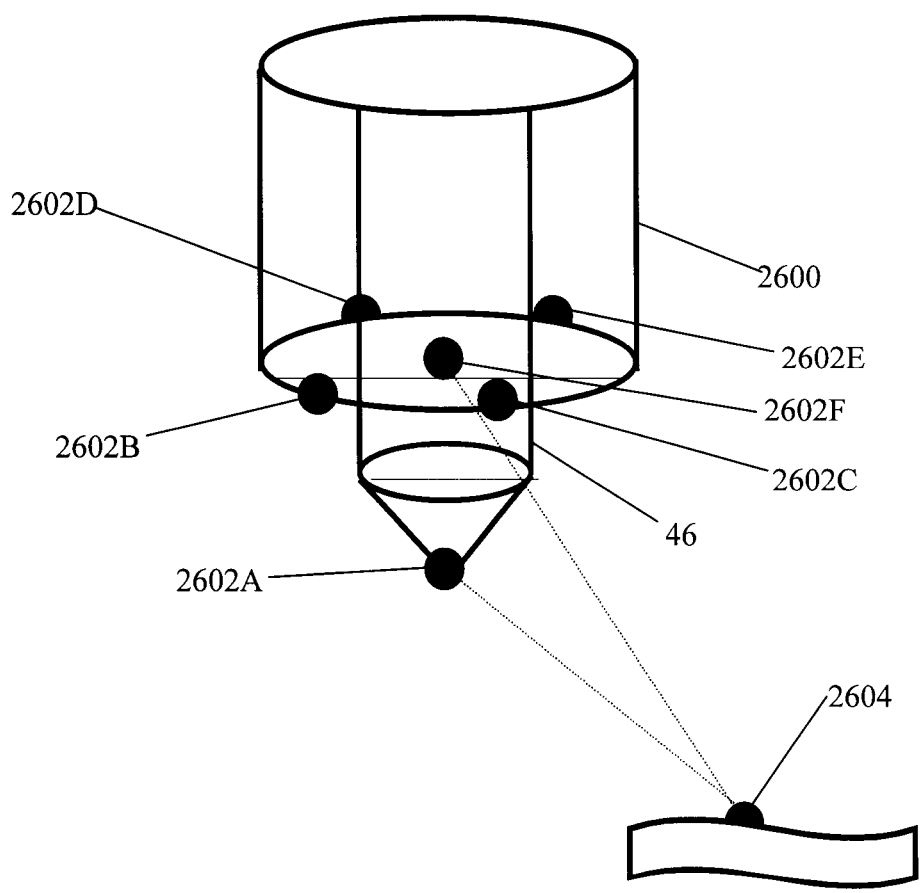
FIG. 26 illustrates a device and a K-wire slidably received in the device with electrodes.

FIG. 26 illustrates a device 2600, such as a cannula 48A in FIG. 16, and a K-wire 46 slidably received in the device 2600. Both the K-wire 46 and the device 2600 have electrodes 2602A-2602F.

Other sets of equations may be similarly derived for alternative electrode geometries. Note that in each case, $i_0$ is eliminated from the calculations. This suggests that the absolute position of the nerve activation site relative to the stimulation electrodes may be calculated knowing only K. As noted above, K is a proportionality constant denoting the relationship between current and distance.

Distance or position of the neural tissue may be determined independent of nerve status or pathology (i.e., elevated $i_0$), so long as stimulation current thresholds can be found for each electrode.

Measuring Nerve Pathology

If the distance to the nerve is known (perhaps through the methods described above), then it is possible to solve equation (8) for $i_0$. This would permit detection of nerves with elevated stimulation thresholds, which may provide useful clinical (nerve pathology) information.

$$i_o = i_{th} - Kd^2 \quad (10)$$

Removing Dependence on K

Figure 24:
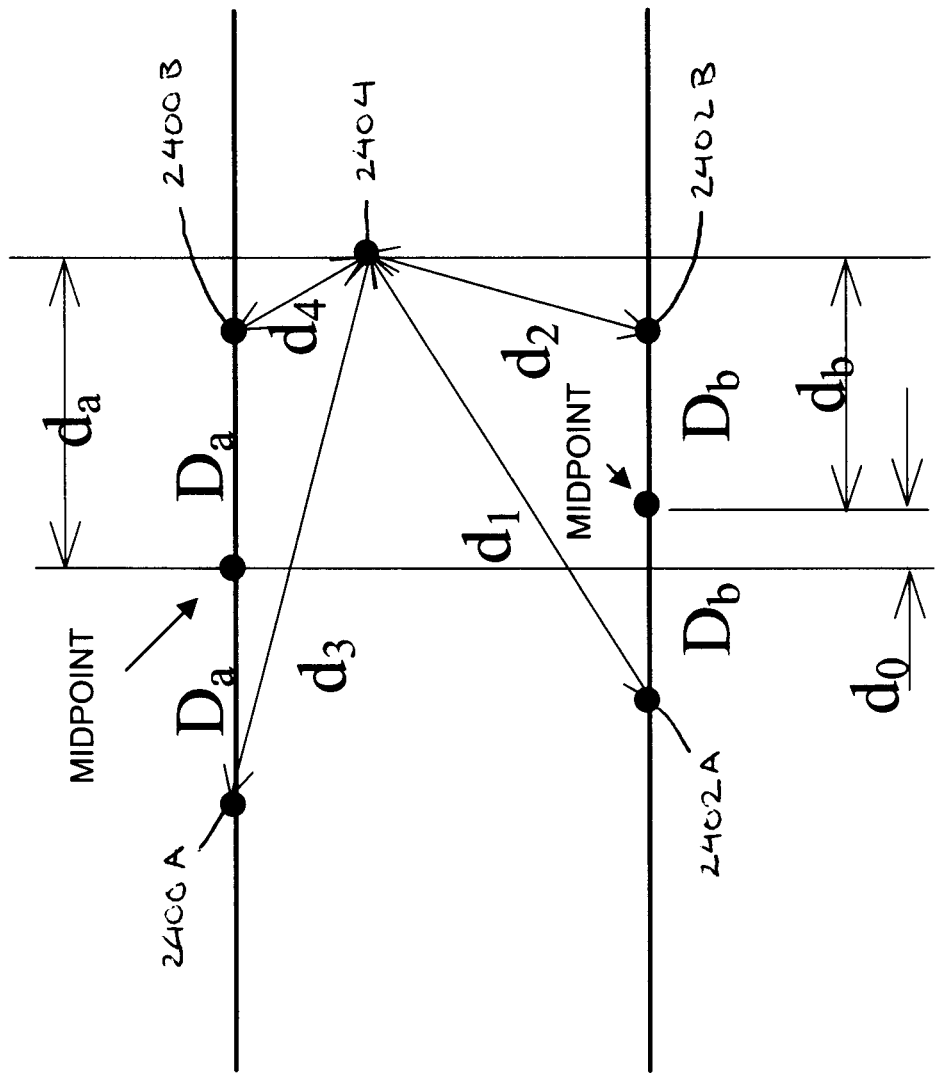
FIG. 24 illustrates a first pair of electrodes in one plane, a second pair of electrodes in another plane and a nerve activation site.

The preceding descriptions assume that the value for K is known. It is also possible to measure distance to a nerve activation site without knowing K, by performing the same measurement from two different electrode sets. FIG. 24 illustrates two pairs of electrodes 2400A, 2400B, 2402A, 2402B and a nerve activation site 2404. The top two electrodes 2400A, 2400B form one pair, and the bottom two electrodes 2402A, 2402B form a second pair. Using the electrodes 2400A, 2400B, 2402A, 2402B and distances defined in FIG. 24, the geometric model from equation (4) becomes:

$$\frac{d_a}{d_b} = \frac{D_b}{D_a}\left(\frac{d_3^2 - d_4^2}{d_1^2 - d_2^2}\right) = \frac{d_0 + d_b}{d_b} = \frac{d_0}{d_b} + 1 \quad (11)$$

Adding the electrical model from equation (7), the dependence on K is removed. Solve equation (11) for $d_b$ to get the distance in one dimension:

$$\frac{D_b}{D_a}\left(\frac{i_3 - i_4}{i_1 - i_2}\right) = \frac{d_0}{d_b} + 1 \quad (12)$$

Finally, it is possible to solve for the value of K itself:

$$K = \frac{i_1 - i_2}{4D_b d_b} \quad (13)$$

Although the configuration in FIG. 14 shows four electrodes, the technique may also work with three collinear electrodes.

Electrode Redundancy

Whichever electrical model is used, the relationship expressed in equation (1) means that the current at any of the electrodes at the four compass points can be "predicted" from the current values of the other three electrodes. Using the electrical model of equation (7) yields:

$$i_w^2 + i_e^2 = i_s^2 + i_n^2$$

Using the electrical model of equation (6) yields:

$$i_w + i_e = i_s + i_n$$

This provides a simple means to validate either electrical model.

Applying the tools of geometric and electrical modeling may help to create more efficient, accurate measurements of the nerve location.

While certain embodiments have been described, it will be appreciated by those skilled in the art that variations may be accomplished in view of these teachings without deviating from the spirit or scope of the present application. For example, the system 22 may be implemented using any combination of computer programming software, firmware or hardware. As a preparatory act to practicing the system 20 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

What is claimed is:

1. A system for finding a direction of a nerve from a surgical instrument comprising:
   a first surgical accessory having at least a first stimulation electrode on a distal region and a second stimulation electrode spaced apart from the first stimulation electrode, the stimulation electrodes each configured to deliver a first set of at least one electrical stimulation signal;
   at least one sensor configured to detect an evoked response from the nerve depolarized by the electrical stimulation signals; and
   a control unit in communication with the first surgical accessory and the at least one sensor, wherein the control unit includes a touch screen display and a base, wherein the touch screen display and the base include at least a processor in communication with a memory, the memory including software instructions, which when accessed by the processor causes the processor to execute the steps of: (a) electrically stimulate the first stimulation electrode with the first set of at least one electrical stimulation signal until a first initial bracket within which a first threshold stimulation current level must lie is determined, (b) electrically stimulate the second stimulation electrode until a second initial bracket within which a second threshold stimulation current level must lie is determined, (c) process the determined first and second initial brackets to find the direction of the nerve from the surgical instrument, said processing including determining the first threshold stimulation current level by narrowing the first initial bracket to a first final bracket and determining the second threshold stimulation current level by narrowing the second initial bracket to a second final bracket, (d) display on the touch screen display an arc indicating a general direction of the nerve from the surgical instrument, the general direction based on the determinations of (i) said first initial bracket and (ii) said second initial bracket, and (e) narrow a length of the arc based on the determinations of (i) said first threshold stimulation current level and (ii) said second threshold stimulation current level, wherein the step of narrowing the length of the arc is indicative of the direction of the nerve from the surgical instrument.

2. The system of claim 1, wherein the first surgical accessory is configured to advance through tissue to create an operative corridor to a surgical target site.

3. The system of claim 2, wherein the first surgical accessory configured to create the operative corridor to the surgical target site is configured to access a spinal target site.

4. The system of claim 3, wherein the first surgical accessory configured to create the operative corridor to the surgical target site is configured to establish the operative corridor via a lateral, trans-psoas approach.

5. The system of claim 1, wherein the surgical accessory comprises at least one of a series of sequential dilation cannulae, and a K-wire.

6. The system of claim 5, wherein the K-wire is slidably received in the surgical accessory.

7. The system of claim 1, further comprising a handle coupled to the first surgical accessory, the handle having at least one button for initiating the first set of at least one electrical stimulation signal from the control unit to the first and second stimulation electrodes on said first surgical accessory.

8. The system of claim 1, wherein the display is further operable to display an electromyographic (EMG) response of a muscle.

9. The system of claim 1, wherein the first surgical accessory further comprises third and fourth stimulation electrodes, each of the first, second, third and fourth electrodes being spaced apart from one another.

10. The system of claim 9, wherein the first second, third, and fourth stimulation electrodes are positioned in a two-dimensional plane.

11. The system of claim 9, wherein the first second, third, and fourth stimulation electrodes are positioned orthogonally to form a cross.

12. The system of claim 11, wherein the control unit is configured to derive x and y Cartesian coordinates of a nerve direction with respect to the first surgical accessory by using $x=i_w^2-i_e^2$ and $y=i_s^2-i_n^2$ where $i_e$, $i_w$, $i_n$, and $i_s$ represent threshold stimulation current levels for the first, second, third, and fourth electrodes, respectively.

13. The system of claim 9, wherein the first, second, third, and fourth stimulation electrodes constitute a first set of electrodes in a first two-dimensional plane and a second set of at least one electrode in another plane that is parallel to the first plane.

14. The system of claim 13, wherein the control unit is configured to determine a three-dimensional vector from a reference point on the surgical accessory to the nerve.

15. The system of claim 14, wherein the control unit is configured to determine the three-dimensional vector from the reference point on the surgical accessory to the nerve by using:

$$x = \frac{1}{4RK}(i_w - i_e)$$

$$y = \frac{1}{4RK}(i_s - i_n) \text{ and } z = \frac{1}{4DK}(i_c - i_k)$$

wherein K is a proportionality constant denoting a relationship between current and distance, R is a cannula radius of the first surgical accessory, $i_e, i_w, i_n$ and $i_s$ represent threshold stimulation current levels for the first, second, third, and fourth electrodes, respectively, $i_k$ is a stimulation current threshold of a k-wire electrode of the first surgical accessory, and $i_c$ is calculated from:

$i_c + KR^2 = \frac{1}{4}(i_w + i_e + i_s + i_n)$.

16. The system of claim 14, wherein the control unit is further configured to display the three-dimensional vector to a user.

17. The system of claim 9, wherein the first second, third, and fourth stimulation electrodes form a tetrahedron.

18. The system of claim 9, wherein the control unit is configured to electrically stimulate the first stimulation electrode with a first electrical stimulation signal of the first set of at least one electrical stimulation signal, determine whether the first threshold stimulation current level has been bracketed, stimulate the second stimulation electrode with a second electrical stimulation signal of the first set of at least one electrical stimulation signal and determine whether the second threshold stimulation current level has been bracketed.

19. The system of claim 18, wherein the first and second electrical stimulation signals are equal.

20. The system of claim 18, wherein the control unit is further configured to determine a first range for the first threshold stimulation current level, and determine a second range for the second threshold stimulation current level, each having a maximum stimulation current threshold value and a minimum stimulation current threshold value.

21. The system of claim 20, wherein the control unit is configured to process the first and second ranges by using $x_{min}=i_{w,min}^2-i_{e,max}^2$; $x_{max}=i_{w,max}^2-i_{e,min}^2$; $y_{min}=i_{s,min}^2-i_{n,max}^2$; $y_{max}=i_{s,max}^2-i_{n,min}^2$, where $i_e$, $i_w$, $i_n$, and $i_s$ represent threshold stimulation current levels for the first stimulation electrode, the second stimulation electrode, the third stimulation electrode, and the fourth stimulation electrode, respectively, wherein $x_{min}$ represents a first component along a first axis, wherein $x_{max}$ represents a second component along the first axis, wherein $y_{min}$ represents a first component along a second axis, wherein $y_{max}$ represents a second component along the second axis, wherein the first axis is orthogonal to the second axis.

22. The system of claim 9, wherein the control unit is further configured to (f) electrically stimulate the third stimulation electrode with a third set of at least one stimulation signal until a third initial bracket within which a third threshold stimulation current level must lie is determined, (g) electrically stimulate the fourth stimulation electrode until a fourth initial bracket within which a fourth threshold stimulation current level must lie is determined, (h) process the determined third and fourth initial brackets to find the direction of the nerve from the surgical instrument, said processing including determining the third threshold stimulation current level by narrowing the third initial bracket to a third final bracket and determining the fourth threshold stimulation current level by narrowing the fourth initial bracket to a fourth final bracket, (i) display on the touch screen display a second arc indicating the direction of the nerve from the surgical instrument, the direction based on the determinations of said third initial bracket and said fourth initial bracket, and (j) narrow a length of the second arc on the touch screen display based on the determinations of said third threshold stimulation current level and said fourth threshold stimulation current level.

23. The system of claim 22, wherein the control unit is further configured to electrically stimulate the third and fourth stimulation electrodes to bisect each of the third and fourth initial brackets until the third threshold stimulation current level has been found for the third stimulation electrode and the fourth threshold stimulation current level has been found for the fourth stimulation electrode within a predetermined range of accuracy.

24. The system of claim 23, wherein the control unit is further configured to electrically stimulate the first, second, third, and fourth stimulation electrodes to bisect each of the first initial bracket, second initial bracket, third initial bracket, and fourth initial bracket until the first threshold stimulation current level has been found for the first stimulation electrode, the second threshold stimulation current level has been found for the second stimulation electrode, the third threshold stimulation current level has been found for the third stimulation electrode, and the fourth threshold stimulation current level has been found for the fourth stimulation electrode within the predetermined range of accuracy.

25. The system of claim 1, wherein the control unit is further configured to electrically stimulate the first and second stimulation electrodes to bisect each of the first and second initial brackets until the first threshold stimulation current level has been found for the first stimulation electrode and the second threshold stimulation current level has been found for the second stimulation electrode within a predetermined range of accuracy.

26. The system of claim 1, wherein the control unit is configured to emit a sound when the control unit determines a distance between the first surgical accessory and the nerve has reached a predetermined level.

27. The system of claim 1, wherein the control unit is configured to emit a sound that indicates a distance between the first surgical accessory and the nerve.

28. The system of claim 1, wherein the first surgical accessory is dimensioned to be inserted percutaneously through a hole to a surgical site.

29. The system of claim 1, wherein the control unit is further configured to determine the first initial bracket and second initial bracket by detecting a response of the nerve depolarized by the first set of at least one electrical stimulation signal and a second set of at least one electrical stimulation signal.

30. The system of claim 1, wherein the first set of at least one stimulation signal comprises stimulation signals of sequentially doubled current intensity.

* * * * *